US012558018B2

(12) United States Patent
Harkema et al.

(10) Patent No.: US 12,558,018 B2
(45) Date of Patent: Feb. 24, 2026

(54) METHODS OF DETECTING AND MAPPING SPINAL CORD EPIDURALLY-EVOKED POTENTIALS

(71) Applicant: University of Louisville Research Foundation, Inc., Louisville, KY (US)

(72) Inventors: Susan J. Harkema, Louisville, KY (US); Ayman El-Baz, Louisville, KY (US); Claudia Angeli, Louisville, KY (US); Samineh Mesbah, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 651 days.

(21) Appl. No.: 16/466,236

(22) PCT Filed: Dec. 12, 2017

(86) PCT No.: PCT/US2017/065714
§ 371 (c)(1),
(2) Date: Jun. 3, 2019

(87) PCT Pub. No.: WO2018/111812
PCT Pub. Date: Jun. 21, 2018

(65) Prior Publication Data
US 2020/0060572 A1      Feb. 27, 2020

Related U.S. Application Data

(60) Provisional application No. 62/432,908, filed on Dec. 12, 2016.

(51) Int. Cl.
*A61B 5/389*      (2021.01)
*A61B 5/00*       (2006.01)
*G06T 5/70*       (2024.01)

(52) U.S. Cl.
CPC ............ *A61B 5/389* (2021.01); *A61B 5/7203* (2013.01); *A61B 5/743* (2013.01); *G06T 5/70* (2024.01)

(58) Field of Classification Search
CPC ....... A61B 5/389; A61B 5/7203; A61B 5/743; A61B 5/7253; A61B 5/407; G06T 5/002
See application file for complete search history.

(56) References Cited

U.S. PATENT DOCUMENTS

2007/0293782 A1      12/2007   Marino
2012/0083647 A1*      4/2012   Scheinin .............. A61N 5/0622
607/101

(Continued)

FOREIGN PATENT DOCUMENTS

KR      2013/0030788      3/2013
KR      1020130030788     3/2013
WO      2013/043157       3/2013

OTHER PUBLICATIONS

Solnik S, Rider P, Steinweg K, DeVita P, Hortobágyi T. Teager-Kaiser energy operator signal conditioning improves EMG onset detection. Eur J Appl Physiol. Oct. 2010;110(3):489-98. doi: 10.1007/s00421-010-1521-8. Epub Jun. 5, 2010. PMID: 20526612; PMCID: PMC2945630. (Year: 2010).*

(Continued)

*Primary Examiner* — Tse W Chen
*Assistant Examiner* — Joseph A Tombers
(74) *Attorney, Agent, or Firm* — Dentons Bingham Greenebaum LLP; Brian W. Chellgren; Natalie F. Beshock

(57)      ABSTRACT

Embodiments of the present invention relate to a novel approach to automatically detect the occurrence of evoked potentials, quantify the attributes of the signal and visualize the effect across a high number of spinal cord epidural stimulation parameters. This new method is designed to (Continued)

automate the current process for performing this task that has been accomplished manually by data analysts through observation of the raw EMG signals, which is laborious and time-consuming as well as being prone to human errors. The proposed method provides fast and accurate framework for activation detection and visualization of the results within five main algorithms.

20 Claims, 23 Drawing Sheets

(56)                    References Cited

U.S. PATENT DOCUMENTS

| 2012/0203123 | A1* | 8/2012 | Mahajan | ................ | A61B 5/024 |
|---|---|---|---|---|---|
| | | | | | 600/509 |
| 2017/0076170 | A1* | 3/2017 | Tuzel | .................... | G06N 5/003 |

OTHER PUBLICATIONS

Extended European search report for application No. EP 17 88 2075 Title: Methods for Detecting and Mapping Spinal Cord Epidurally Evoked Potentials.
International Preliminary Report on Patentability, International application No. PCT/US2017/065714, Applicant University of Louisville Research Foundation, Inc., issued Jun. 18, 2019.
International Search Report and Written Opinion, mailed Mar. 15, 2018—International Application No. PCT/US2017/065714.

* cited by examiner

METHODS OF DETECTING AND MAPPING SPINAL CORD EPIDURALLY-EVOKED POTENTIALS

This application claims the benefit of U.S. provisional patent application Ser. No. 62/432,908, filed 12 Dec. 2016, for METHODS FOR DETECTING AND MAPPING SPINAL CORD EPIDURALLY-EVOKED POTENTIALS, incorporated herein by reference.

FIELD OF THE INVENTION

Embodiments of the present invention relate to a novel approach to automatically detect the occurrence of evoked potentials, quantify the attributes of the signal and visualize the effect across a high number of spinal cord epidural stimulation parameters. This new method is designed to automate the current process for performing this task that has been accomplished manually by data analysts through observation of the raw electromyography (EMG) signals, which is laborious and time-consuming as well as being prone to human errors. The proposed method provides fast and accurate framework for activation detection and visualization of the results within five main algorithms.

BACKGROUND

This invention relates in general to detection of evoked potentials in the field of lumbosacral spinal cord epidural stimulation. Previously it has been shown that epidural electrical stimulation with a combination of locomotor training and/or pharmacological interventions in animal models was able to highly promote spinal circuits functionality after complete spinal cord transections in rats. Subsequently, in the past several years, clinical studies have also reported that lumbosacral spinal cord epidural stimulation (scES) combined with activity-based training progressively re-enabled full weight bearing standing and volitional control of lower limbs in individuals with chronic complete paralysis. Remarkably, the appropriate selection of stimulation configuration (amplitude, pulse width, frequency and anode/cathode assignment) was shown to be critical to promote the generation of effective motor patterns. Mapping experiments were initially performed with participants in supine position, recording motor evoked potentials from different lower limb muscles using surface EMG during scES with different sets of electrode configuration, in order to study the topographical features of recruiting leg muscles by scES and also to provide useful information for the selection of electrode configurations applied for promoting lower limb motor function. EMG is a diagnostic procedure that uses electrodes to detect electrical signals transmitted by motor neurons that cause muscles to contract. The task of determining the links between scES parameters and the characteristics of the evoked potentials detected by EMG is referred to as "mapping" task in this study.

To study the characteristics of the scES induced evoked potentials, the first step is to localize them inside raw EMG signals that are recorded from several leg muscles by segmenting each EMG signal based on the stimulation onset. The precise detection of each epidurally evoked potential in order to determine the effective threshold for scES intensity that triggered the occurrence of the first visible evoked potential for each muscle, is one of the most challenging tasks in the EMG analysis in the scES content. This task is usually performed by visual inspection by a trained observer, which is considered to be the most accurate method for activation detection. However, it is a laborious task when facing a great stack of data recorded from several muscles during various experiments and therefore can be prone to human errors and also would limit the ability to allow scalability to a high number of patients. Therefore, to facilitate the activation detection process, an accurate computer-based method is proposed in this work.

There have been several methods proposed for computer-based change detection for EMG signals in the literature such as single or double threshold detector, Teager-Kaiser Energy Operation, wavelet template matching, supervised and unsupervised learning algorithms or statistical criterion determination methods like hidden Markov models (HMM) or Gaussian mixture models (GMM). The main goal of all such methods is to convert the original raw signals into a set of estimated sequences that make the highest distinction between the signals before and after change and detect the occurrence of the change and the corresponding time instant $t=0$ as early as possible.

Most of the automatic onset detection methods can be divided into three main stages: conditioning, decision threshold, and post-processing. In the conditioning stage, the EMG signal goes through a test function, which is a type of event indicator. In the second stage, the algorithm will set a threshold that indicates the first point of the signal change. Finally, the last stage deals with the false alarms by setting certain constraints on the detected onset values. Most of the methods differ based on the type of test function, the decision rule, which involves the selection of constant or dynamic thresholds, and the heuristic constraints for the final detected onset, which varies based on the application and the characteristics of the EMG signals. There are several categories for the event indicator function such as on-line versus off-line, or supervised versus unsupervised learning algorithms. If an algorithm is causal, meaning that it operates only based on current and previous samples of the signal and not the future values, the method is called on-line, otherwise it is considered off-line. Also, if the training input data for a learning method is already labeled using a priori information, the method is supervised, and if the algorithm estimates a model for the input data using certain parameter estimation techniques, it is an unsupervised technique.

In every activation detection method, sensitivity to the noise level in the signal is a great challenge. Selection of a proper conditioning and post-processing method usually helps to minimize the effect of noise on the accuracy of the method. It is also notable that some of the proposed methods, i.e. supervised methods, are highly dependent on the prior information about the signal which makes those methods semi-automatic and their accuracy application-dependent.

SUMMARY

Voluntary movements and standing of spinal cord injured patients have been facilitated using lumbosacral scES. Identifying the appropriate stimulation configurations (amplitude, pulse width, frequency, and anode/cathode assignment) is an arduous task and requires extensive mapping of the spinal cord using evoked potentials. Effective visualization and detection of muscle evoked potentials induced by scES from the recorded EMG signals is critical to identify the optimal configurations and to understand the effect of specific scES parameters on muscle activation. The present invention is a novel method for automatically detecting the occurrence of evoked potentials, quantifying the attributes of the signal and visualizing the effect across a high number of scES parameters. This new method is designed to automate the current process for performing this task that has been accomplished manually by data analysts through observation of the raw EMG signals, which is laborious and time-consuming as well as being prone to human errors. The proposed method provides fast and accurate framework for activation detection and visualization of the results within five main algorithms. The first algorithm converts the one-dimensional EMG signal into its 2-D representation by overlaying the located signal activation building blocks. Second, the Generalized Gaussian Markov Random Field (GGMRF) technique is applied to the constructed 2-D EMG representation to de-noise the EMG signal. Thirdly, the evoked potentials are detected using a statistically optimal maximum likelihood estimator together with comparing the probability density functions of the muscle activations to the background noise utilizing a log-likelihood ratio. Fourthly, several features of the motor units such as peak-to-peak, latency, integrated EMG and Min-max time intervals are extracted from the evoked muscle responses. Finally, the extracted features are visualized as Colormap images or another convenient form of chart, graph or table. In comparing the automatic method vs. manual EMG processing on more than 700 EMG signals from five individuals, the new automated approach decreased the processing time from several hours to less than 15 seconds for each set of data, and demonstrated an averaged accuracy of 98.28% based on the combined false positive and false negative error rates. The sensitivity of the new method to signal to noise ratio was tested using simulated EMG signals and compared to two existing methods, where the novel technique showed much lower sensitivity to signal to noise ration. In conclusion, this study clearly demonstrates the advantages of the proposed approach for improving the accuracy and speed in complex data analysis.

Disclosed herein is a novel method that addresses the two main challenges that a fully automatic activation detection method is facing by proposing an unsupervised and on-line approach that deals with the stochastic characteristics of the EMG signals in the scES application. This novel method is adapted to automatically detect epidurally evoked potentials using a general framework in the context of scES-EMG mapping and is able to effectively de-noise, detect, extract the key features and visualize the occurrence of muscle evoked potentials that are induced by scES and increase the accuracy and efficiency of the physiological mapping process in order to determine the underlying relationships between the scES parameters and muscle activations. Consequently, this framework assists the data analysts to promptly decide on further adjustments or improvements in designing future experiments.

This summary is provided to introduce a selection of the concepts that are described in further detail in the detailed description and drawings contained herein. This summary is not intended to identify any primary or essential features of the claimed subject matter. Some or all of the described features may be present in the corresponding independent or dependent claims, but should not be construed to be a limitation unless expressly recited in a particular claim. Each embodiment described herein is not necessarily intended to address every object described herein, and each embodiment does not necessarily include each feature described. Other forms, embodiments, objects, advantages, benefits, features, and aspects of the present invention will become apparent to one of skill in the art from the detailed description and drawings contained herein. Moreover, the various apparatuses and methods described in this summary section, as well as elsewhere in this application, can be expressed as a large number of different combinations and subcombinations. All such useful, novel, and inventive combinations and subcombinations are contemplated herein, it being recognized that the explicit expression of each of these combinations is unnecessary.

BRIEF DESCRIPTION OF THE DRAWINGS

A better understanding of the present invention will be had upon reference to the following description in conjunction with the accompanying drawings.

FIG. 2A is a graph depicting a raw EMG signal. FIG. 2B is a graph illustrating segmentation of the raw EMG signal using stimulation time intervals. FIG. 2C is a 3-D graph depicting the overlaid segments, wherein the X-axis is the evoked potentials duration ($\mu$s), the Y-axis is the stimulation voltage (V), and the Z-axis is the amplitude of the signals ($\mu$V). FIG. 2D is a 2-D Colormap image depicting the data of the 3-D graph in FIG. 2C, wherein the X-axis is the evoked potentials duration ($\mu$s), the Y-axis is the stimulation voltage (V), and the amplitude of the signals ($\mu$V) is indicated by the color of the image.

FIG. 3A depicts the 2-D Colormap image of FIG. 2D with an overlaid representation of the application of the GGMRF method. FIG. 3B is a graph depicting the EMG signal before and after application of the GGMRF method.

FIG. 4A is a graph depicting an evoked potential in a single segment of the EMG signal. FIG. 4B is a graph depicting the evoked potential of FIG. 4A with a histogram of its estimated Gaussian distribution. FIG. 4C is a graph comparing the Gaussian probability density function (PDF) of evoked potential signal to the PDF of background noise. FIG. 4D is a graph plotting the calculated the log-likelihood ratio (LLR) for each segment of the EMG signal and determining the activation threshold.

FIG. 5A depicts the Colormap image of FIG. 2D with the number of peaks of the evoked potential, activation onset and latency identified by visual inspection. FIG. 5B is a graph depicting features extracted by an embodiment of the automated method of the present invention, namely, the peak-to-peak value (Vpp), activation latency, time interval between minimum and maximum values (Tpp) and integrated EMG (summation of absolute values of all gray areas).

FIG. 7A depicts a comparison of accuracy. FIG. 7B depicts a comparison of sensitivity. FIG. 7C depicts a comparison of specificity. FIG. 7D depicts a comparison of Dice similarity.

FIG. 9A depicts the peak-to-peak amplitude of detected evoked potentials as a function of muscles vs. stimulation voltage for a given frequency and configuration. FIG. 9B depicts the peak-to-peak amplitude as a function of configuration vs. stimulation voltage for a given muscle and frequency. FIG. 9C depicts the integrated EMG values as a function of muscles vs. stimulation frequency for a given voltage and configuration. In these images, the gray area represents the pre-threshold part of the experiment where no activation was induced. In the graphical representation of the configurations, cathodes are black, anodes are gray and un-assigned electrodes are white.

DETAILED DESCRIPTION OF THE PREFERRED EMBODIMENTS

Figure 1:
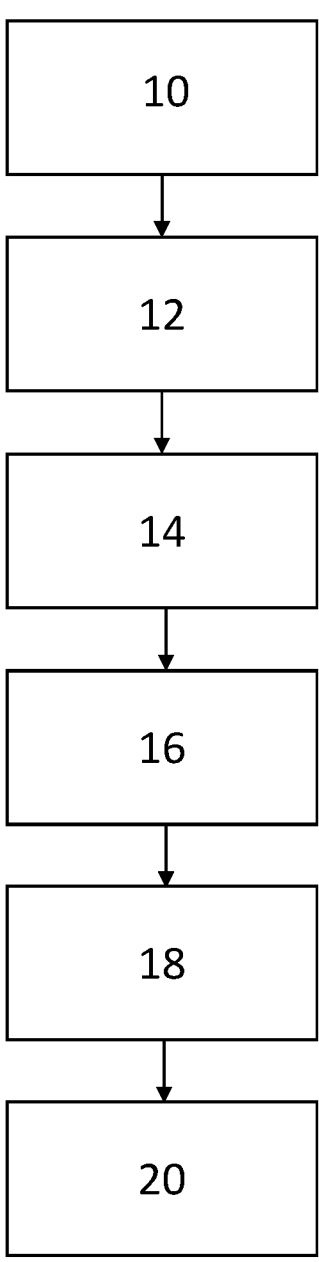
FIG. 1 depicts a block diagram of the proposed framework for visualization and onset detection of muscle activations induced by epidural spinal cord stimulation in individuals with spinal cord injury.

For the purposes of promoting an understanding of the principles of the invention, reference will now be made to selected embodiments illustrated in the drawings and specific language will be used to describe the same. It will nevertheless be understood that no limitation of the scope of the invention is thereby intended; any alterations and further modifications of the described or illustrated embodiments, and any further applications of the principles of the invention as illustrated herein are contemplated as would normally occur to one skilled in the art to which the invention relates. At least one embodiment of the invention is shown in great detail, although it will be apparent to those skilled in the relevant art that some features or some combinations of features may not be shown for the sake of clarity.

Any reference to "invention" within this document is a reference to an embodiment of a family of inventions, with no single embodiment including features that are necessarily included in all embodiments, unless otherwise stated. Furthermore, although there may be references to "advantages" provided by some embodiments of the present invention, other embodiments may not include those same advantages, or may include different advantages. Any advantages described herein are not to be construed as limiting to any of the claims.

Specific quantities (spatial dimensions, dimensionless parameters, etc.) may be used explicitly or implicitly herein, such specific quantities are presented as examples only and are approximate values unless otherwise indicated. Discussions pertaining to specific compositions of matter, if present, are presented as examples only and do not limit the applicability of other compositions of matter, especially other compositions of matter with similar properties, unless otherwise indicated.

In some embodiments, the present invention is a method for detection and characterization of evoked potentials in muscles comprising multiple steps. Referring now to FIG. 1, in an initial step 10, epidural stimulation is applied to a patient and an electrical signal evoked from the patient's muscle in response to the epidural stimulation is detected by EMG or other suitable diagnostic process. In a first step 12, the electrical signal is temporally segmented into sequential segments. In a second step 14, image processing techniques are applied to the signal to reduce signal noise. In a third step 16, evoked potentials are detected within the electric signal. In a fourth step 18, features of the evoked potentials are extracted. In a fifth step 20, the evoked potentials are converted into a graphical form for ease of visualization by analysts. Each of these steps are described in further detail below.

2. Materials and Methods

Participants: In this study, five male individuals with motor complete SCI participated. Two of these participants have AIS grade B and three of them have AIS grade A. The average age of these five individuals at the time of the experiments was 29.82±4.458 years old and the average time since injury was 4.22±1.553 years.

Spinal Cord Epidural Stimulation: A stimulation unit in combination with a chronical 16-electrode array was surgically implanted at the T11-L1 vertebral levels over the spinal-cord segments L1-S2. It was used to deliver electrical stimulation to the lumbosacral spinal cord of each SCI individual. The scES lower limbs mapping experiments started 2-3 weeks after the surgical implantation.

2.1 EMG Data Acquisition

The supine experiments were performed with the participants relaxed in a supine position. The electrical stimulation waveform had a rectangular, biphasic shape with pulse duration of 450 μsec. In each experiment a particular combination of electrode array is selected to activate, which is referred to as the stimulation configuration. A total of 12 different stimulation configurations were examined for each individual. For each configuration, the scES intensity (in volts) was increased while the frequency (in hertz) was fixed at (2 Hz). This allowed a simple evoked potential as well as a reasonable time frame in which to complete the experiments. During each intensity ramp up, the scES intensity started at a pre-threshold value and increased with 0.1 or 0.5 V increments up to 10 V. scES delivered a minimum of five stimulus pulses at each intensity level. During the performance of each experiment, the surface EMG signals were recorded from 14 leg muscles, using bipolar surface electrodes that were placed on the left (L) and right (R) soleus (SOL), medial gastrocnemius (MG), tibialis anterior (TA), vastus lateralis (VL), rectus femoris (RF), medial hamstrings (MH), and gluteus maximus (GL). The recorded EMG signals were digitized with a sampling rate of 2000 samples per second. In addition, two more surfaced electrodes were placed laterally over the paraspinal muscles in order to record the onset of the stimulus.

2.2 Methodology

In this section, a set of five algorithms is proposed for the mapping task in order to convert the raw recorded EMG signal into its significant building blocks, which are evoked potentials induced by ES, and extract several features of these evoked potentials and visualize them in order to effectively represent the desired hidden information in the EMG records to the data analysts. Moreover, the pseudocode of each step of the framework is presented below.

2.2.1 2-D Representation of EMG Signal

Figure 2A:
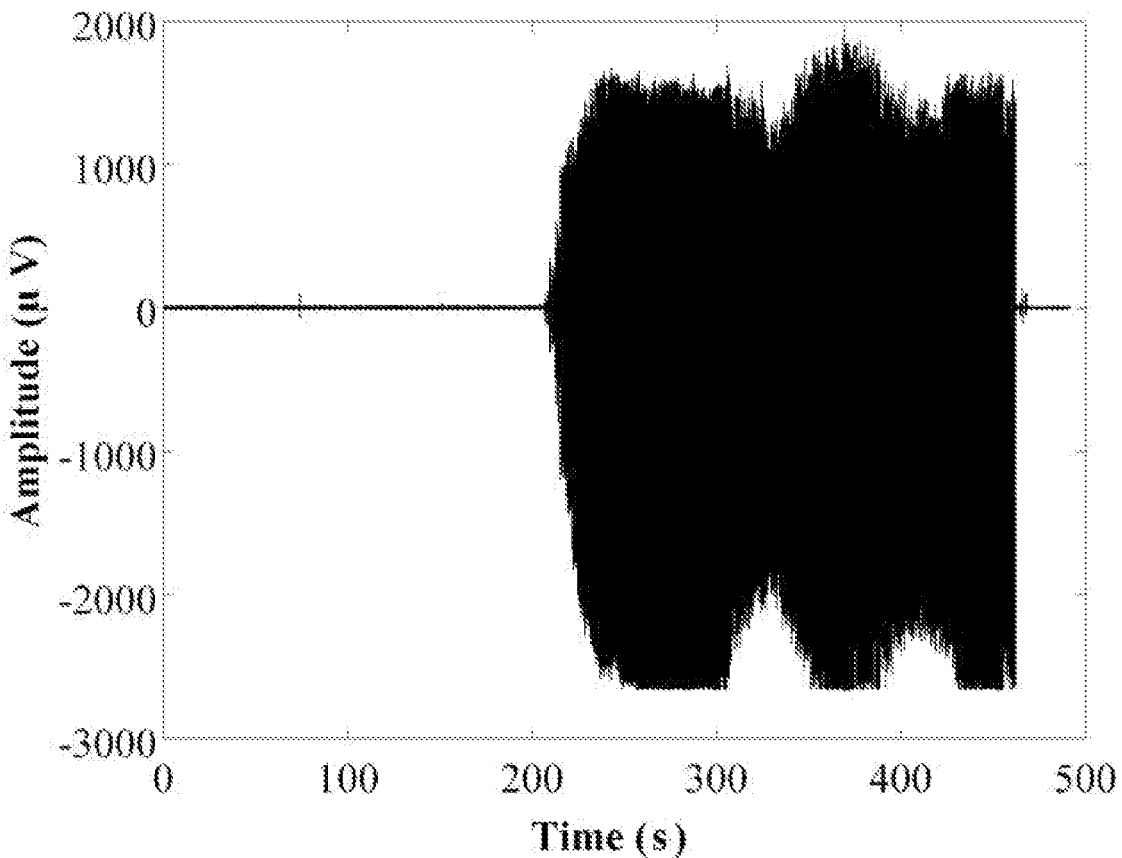
FIGS. 2A-D depict the steps for converting raw EMG signals into 2-D and 3-D images.
Figure 2B:
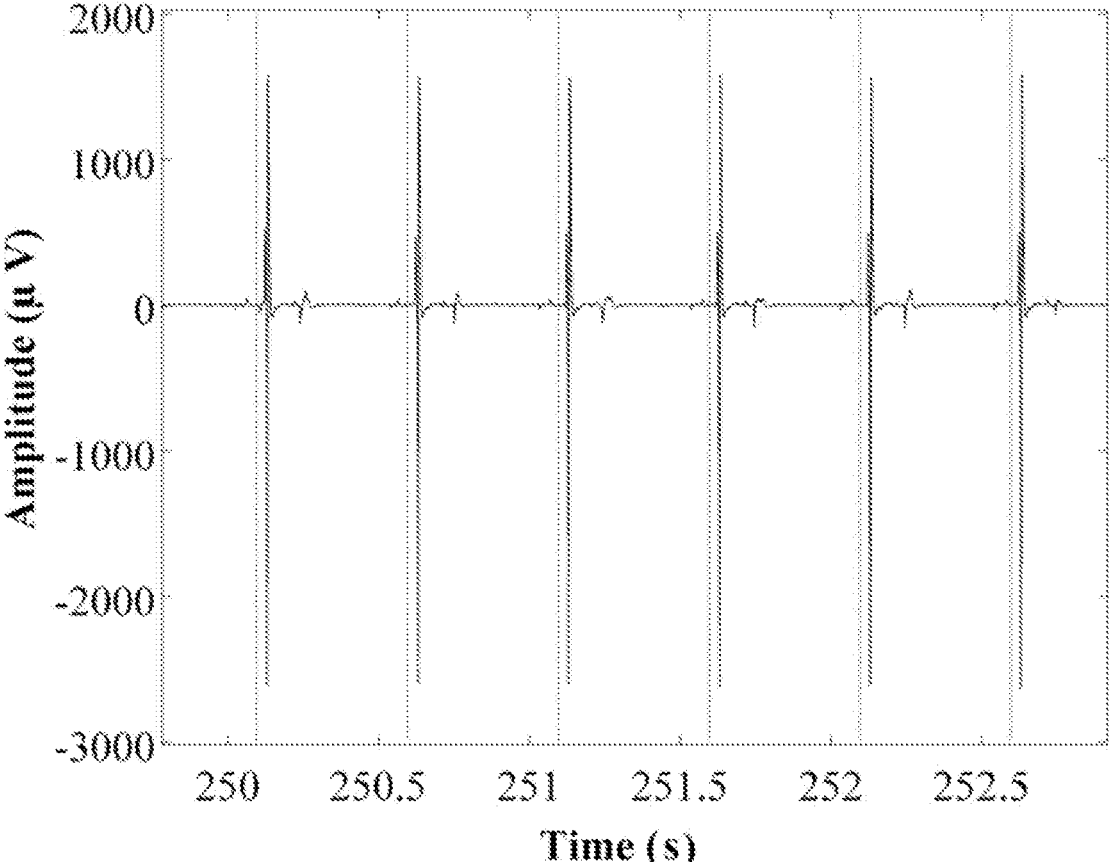
Figure 2C:
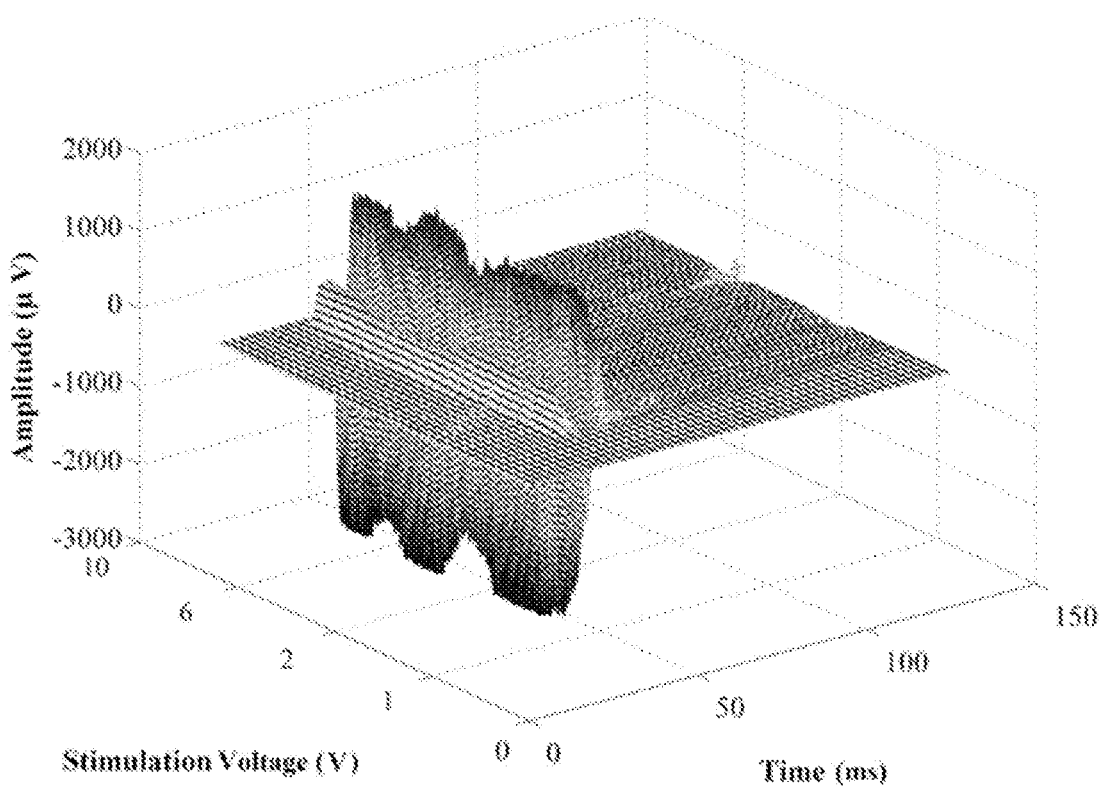
Figure 2D:
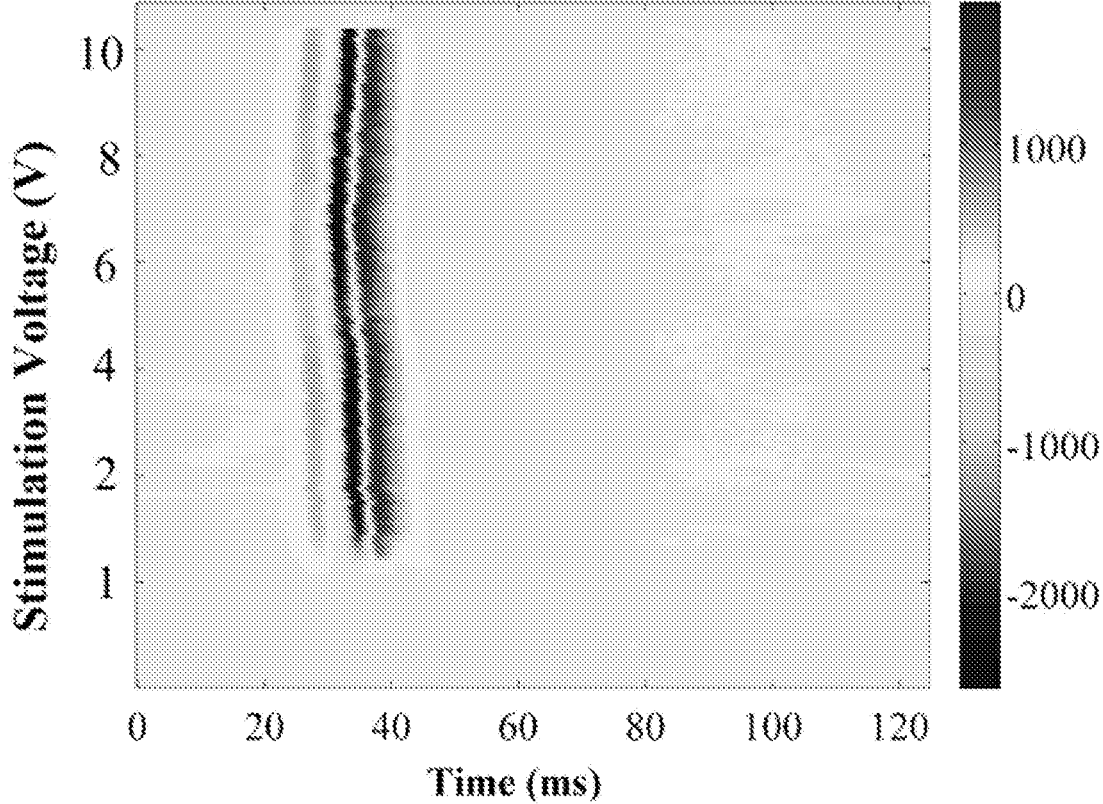

From a computational point of view, each single record of the EMG $(x\_k, k \geq 1)$ is a set of sample observations of a discrete random process $(X\_k, k \geq 1)$. The EMG signals, which were recorded from leg muscles during supine experiments, consist of evoked potentials $(w\_1, w\_2, \ldots, w\_N \epsilon W)$, which were induced by ES, and the corresponding stimulation onset timings $(t\_i)$, are marked using the paraspinal muscles signals. Utilizing this information, the whole EMG signal can be segmented into its building blocks (W set) where each segment is the time interval between two consecutive stimulation pulsations (FIG. 2A, 2B). Subsequently, the first algorithm converts the EMG signal, $X\_k$, to a 3-D image, $\delta\_k$ $(x,y,z)$, by overlaying all these EMG portions and then showing their value in 3-D graphs (FIG. 2C). By using the Colormap technique, a 3-D graph can be converted to a 2-D image where the amplitude values are represented by colors (FIG. 2D). Each row in the Colormap image is one segment of the whole EMG signal (Algorithm I, below).

---

Algorithm I: 2-D representation of the raw EMG signals

---

Find the time intervals between each two consecutive stimulation
pulsations using the onset timing of each stimulation
Use the time intervals to segment the EMG signals into corresponding
pieces
Repeat for all the muscles
Save the samples of EMG segments into a m × n × l matrix where m
is the number of stimulation pulsation, n is the maximum time interval
between consecutive stimulations, and l is the number of muscles.
(Optional) Visualize the m × n matrix as Colormap image (use MATLAB
imagesc function or equivalent)
Repeat for all muscles

---

2.2.2 Noise Reduction

Figure 3A:
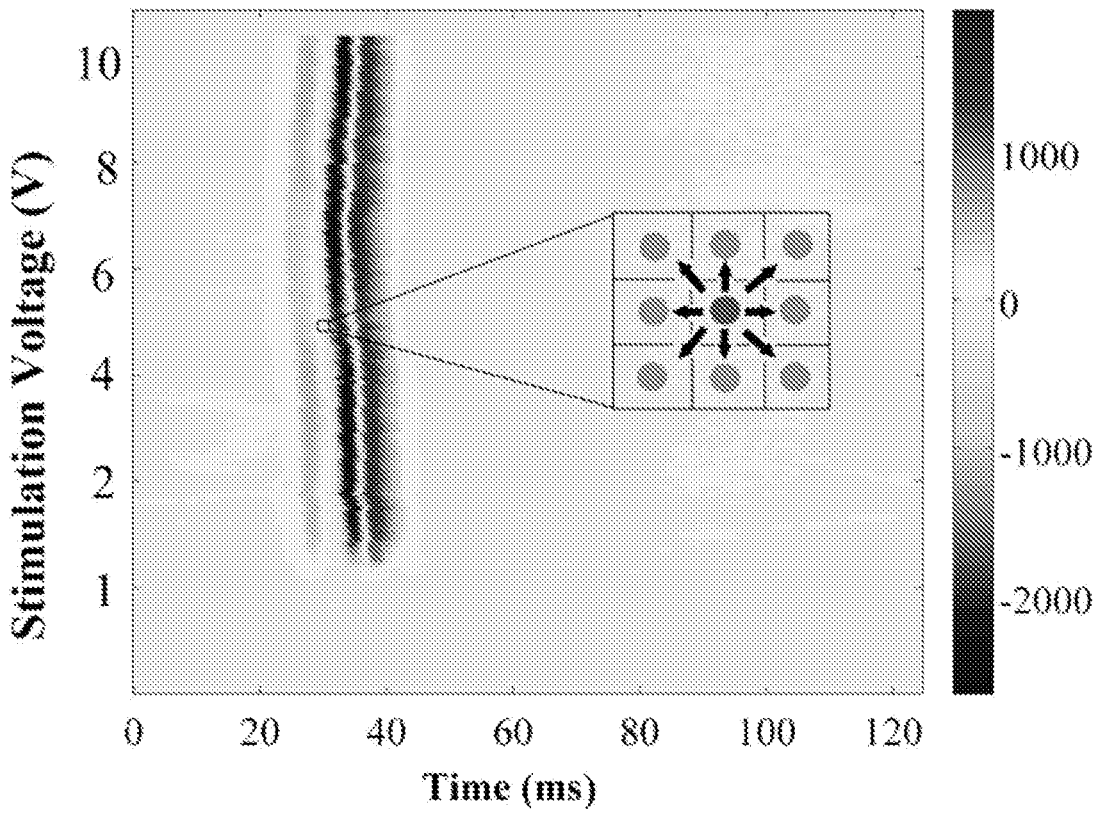
FIGS. 3A-B depict application of the GGMRF method to reduce signal noise.
Figure 3B:
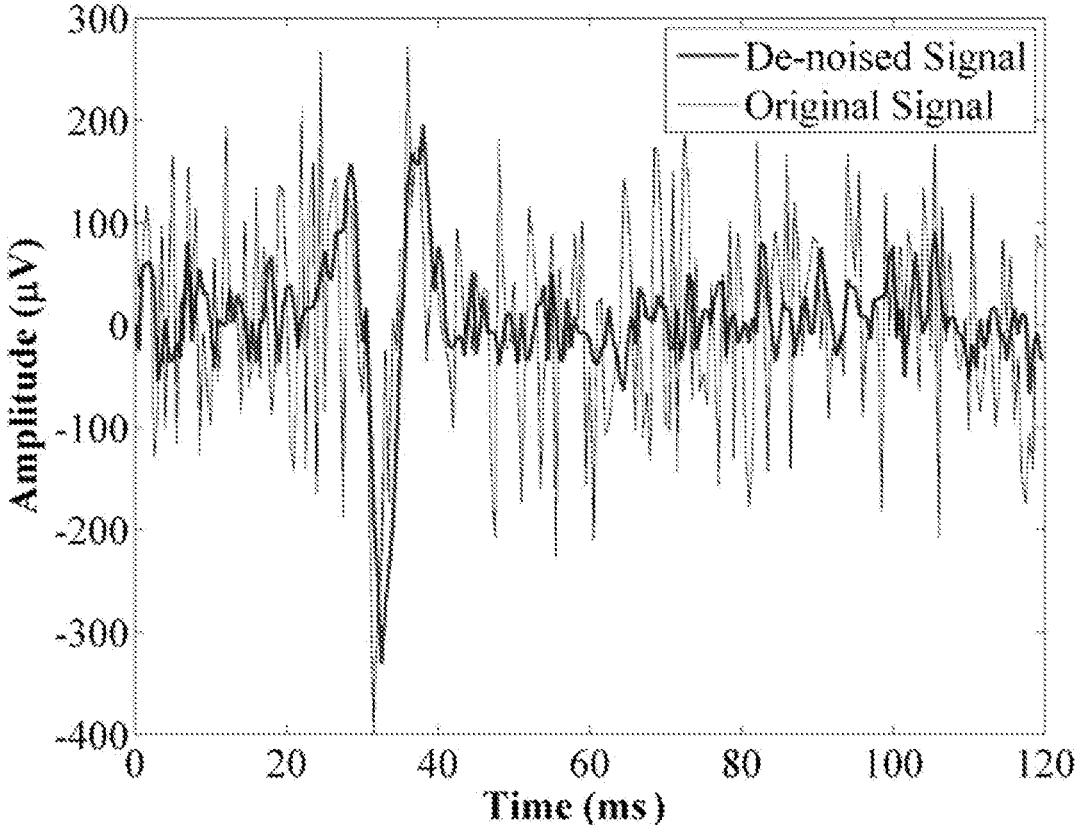

After signal to image conversion, it is possible to use image-processing techniques for smoothing the images and consequently de-noising the signals. The 2-D generalized Gaussian Markov Random Field (GGMRF) model was applied to the constructed 2-D images so as to reduce the noise level from the EMG signal. This is an image smoothing method, which preserves continuity and removes inconsistencies in the image that in this context is caused by background noise in the original EMG signals. In this method, each pixel's value, which is the evoked potential amplitude in $\mu V$, is being compared to 8-neighborhood pixel set and recalculated using Equation 2.1.

$$\hat{\delta}_s = \underset{\delta_s}{\mathrm{argmin}}\left\{ |\delta_s - \tilde{\delta}_s|^q + \sigma^{-q}\lambda^p \sum_{r \in v_s} b_{s,r}|\tilde{\delta}_s - \delta_r|^p \right\} \qquad \text{Equation 2.1}$$

Where $\delta_s$, $\hat{\delta}_s$ and $\tilde{\delta}_s$ are original pixel value, its recalculated value, and expected estimate respectively. $v_s$ is the 8-neighborhood pixel set; $b_{s,r}$ is the GGMRF potential; and a and $\lambda$ are scaling factors. The parameter $p \epsilon [1.01, 2.0]$ controls the smoothing level (e.g., p=2 for smooth versus p=1.01 for relatively abrupt edges). The parameter $q \epsilon \{1, 2\}$ determines the Gaussian (q=2) or Laplace (q=1) prior distribution of the estimator. Our simulations were conducted with $\sigma=1$, $\lambda=5$, p=1.01, q=2, and $b_{s,r}=\sqrt{2}$. An example of the input and output of the GGMRF method and their corresponding muscle activation segments is demonstrated in FIG. 3 (Algorithm II, below).

---

Algorithm II: Noise reduction

---

Initialize the GGMRF parameters $\sigma$, $\lambda$, p, q, and $b_{s,r}$ for Eq. 2.1
Determine the window size for the Eq. 2.1
Design an all ones m × n mask matrix and set its four borders
rows and columns to zero
Use m × n segmentation matrix, m × n mask matrix, parameters
and window size to substitute in Eq. 2.1 and calculate the estimated
value for the pixel
Repeat for all pixels
Repeat for all muscles

---

The advantage of spatial smoothing of EMG signals, compared to the traditional signal low pass and high pass filtering techniques, is that this method offers the option of comparing each evoked potential with the previous and the next activation, and it reduces the signal irregularities that are caused by different sources of noise. Unlike the filtering methods, the image smoothing method offers a de-noised signal without any significant changes in the position and original shape of muscle activations.

2.2.3 Activation Detection

The activation detection algorithm is designed to determine the presence or absence of scES induced evoked potentials in each segment of the EMG signals and consequently the corresponding stimulation intensity threshold. The pre-assumptions for this task are: 1) The intensity threshold Vs0, which caused the earliest evoked potential, is an unknown random value with unknown distribution; 2) The amplitude of the first visible evoked potential is also an unknown value. These are valid assumptions because of the non-stationary nature of EMG signals and the fact that no a priori information about the distribution of the changing parameters is present. It is also notable that these onset values are highly variable and alter based on the choice of stimulation configuration, frequency, muscle type, and also depending on the day-to-day and pre-post training variability. As mentioned above, scES delivers the minimum of five pulse stimulations at each stimulus voltage referred to as an event, $(w_{i+j}, 0 \leq j \leq N_i)$ where $\min(N_i)=5$. Therefore, it is assumed that if at least 50 percent of the EMG segments corresponding to the same stimulation intensity show epidurally evoked potentials, that intensity will be considered as the intensity threshold $V_{s0}$.

Figure 4A:
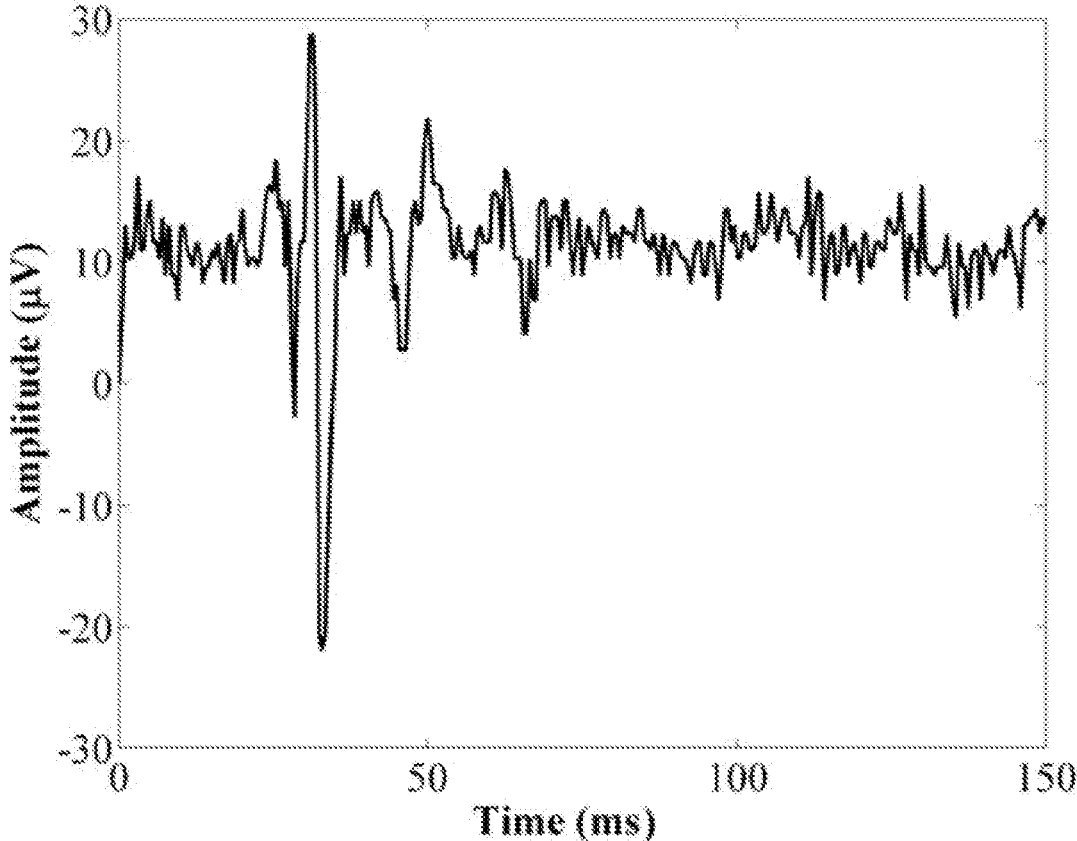
FIGS. 4A-D depict calculation steps for the activation detection algorithm.
Figure 4B:
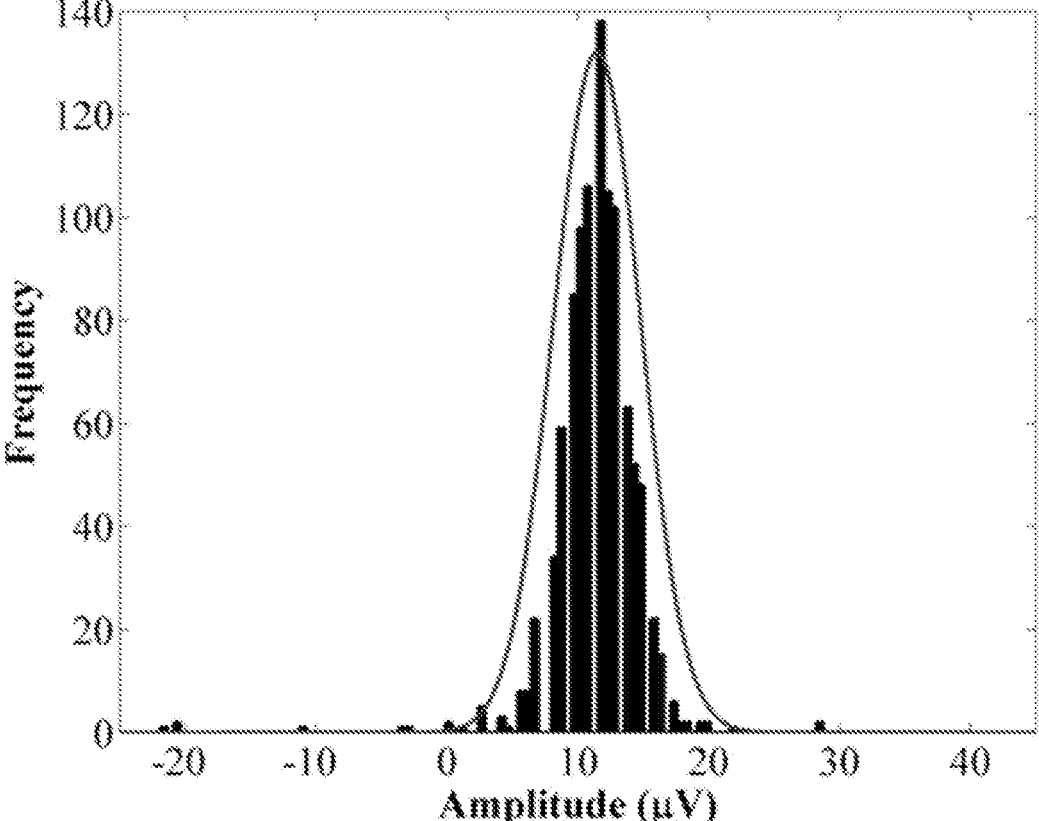
Figure 4C:
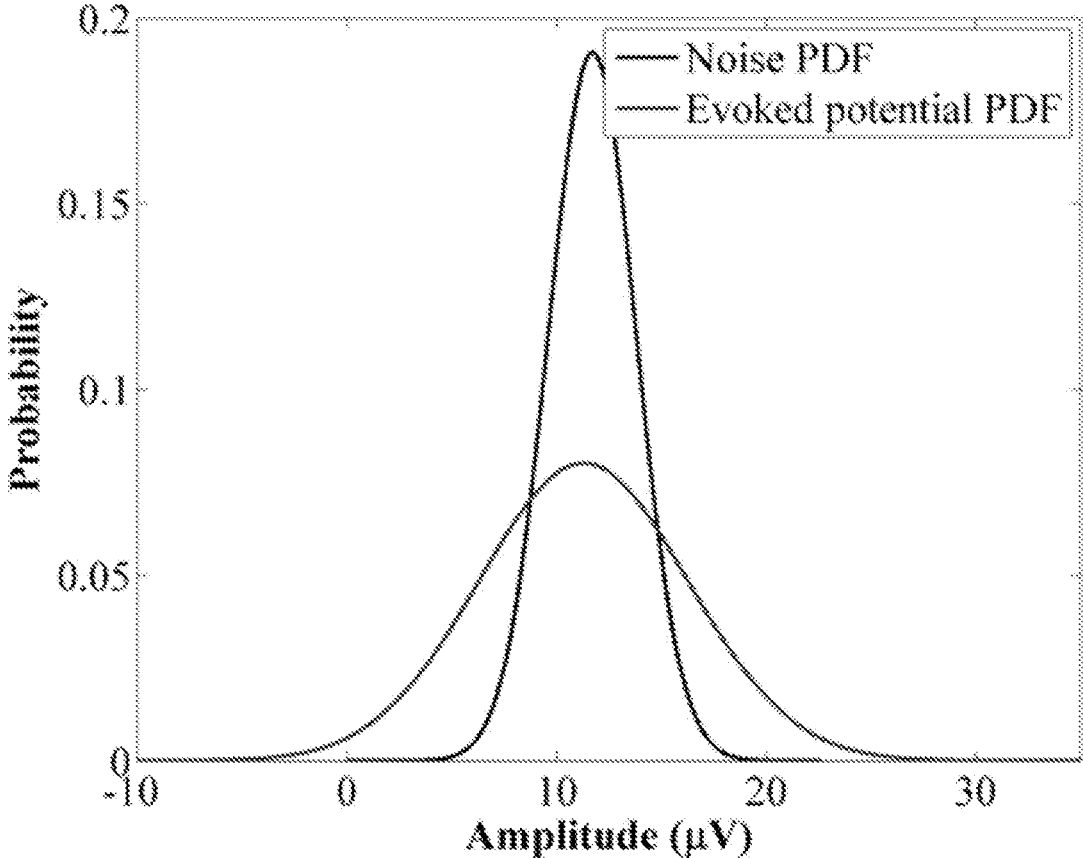

The general technique implemented in this step is known as the statistically optimal decision (SOD) method. One derivation of SOD is the approximated generalized likelihood-ratio (AGLR) detector. Here, this method is modified and adapted to the present activation detection application. The modified method has three main phases. In the first phase, each segmented and de-noised portion of the signal $(w\_i \epsilon W)$ is modeled by a Gaussian probability density function (pdf) and the model parameters $\mu_i$ and $\sigma_i$ are estimated using the maximum likelihood estimation (MLE) method $(p_\theta(w_i))$. FIG. 4B shows the histograms of the one segment of the EMG and its estimated Gaussian distribution. From the statistical point of view, the activation detection method represents a binary selection between the null hypothesis H0 that says "there is no significant change in the pdf $p_{\theta_0}(w_i)$ of the $i^{th}$ segment of the signal" and the alternate hypothesis that says "there is a significant change in the parameters of pdf $p_{\theta_1}(w_i)$." Therefore, in the second phase, the Gaussian model of all the EMG segments will be compared to the Gaussian model of the background noise by the log-likelihood ratio (LLR) measure. Eq. 2.2 shows the general formulation of the LLR.

$$s_k = \ln\left(\frac{p_{\theta_1}(y_{i_k})}{p_{\theta_0}(y_{i_k})}\right) \qquad \text{Equation 2.2}$$

Where $y_{i_k}$ is the $k^{th}$ sampled-value of $w_i$ segment. In order to reduce the high computational cost of this equation, it is presupposed that the occurrence of the scES induced muscle activation does not change the mean $\mu$ of the Gaussian pdf and the most significant changes happen in the standard deviation $\sigma_i$ of the pdf as shown in FIG. 4C. Therefore, the Eq. 2.2 is modified and simplified herein to Eq. 2.3.

$$s_k = \ln\left(\frac{\sigma_0}{\sigma_i}\right) + \frac{1}{2}(y_{i_k} - \mu)^2\left(\frac{1}{\sigma_0^2} - \frac{1}{\sigma_i^2}\right) \qquad \text{Equation 2.3}$$

The sum of all the $s_k$ values over one segment is referred to as CUSUM value $S_i$ and is calculated based on Eq. 2.4.

$$S_i = \sum_{k=j}^{N_i} s_k = (N_i - j + 1)\ln\left(\frac{\sigma_0}{\sigma_i}\right) + \frac{(N_i - j)}{2}\left(\frac{\sigma_i^2}{\sigma_0^2} - 1\right) \qquad \text{Equation 2.4}$$

Figure 4D:
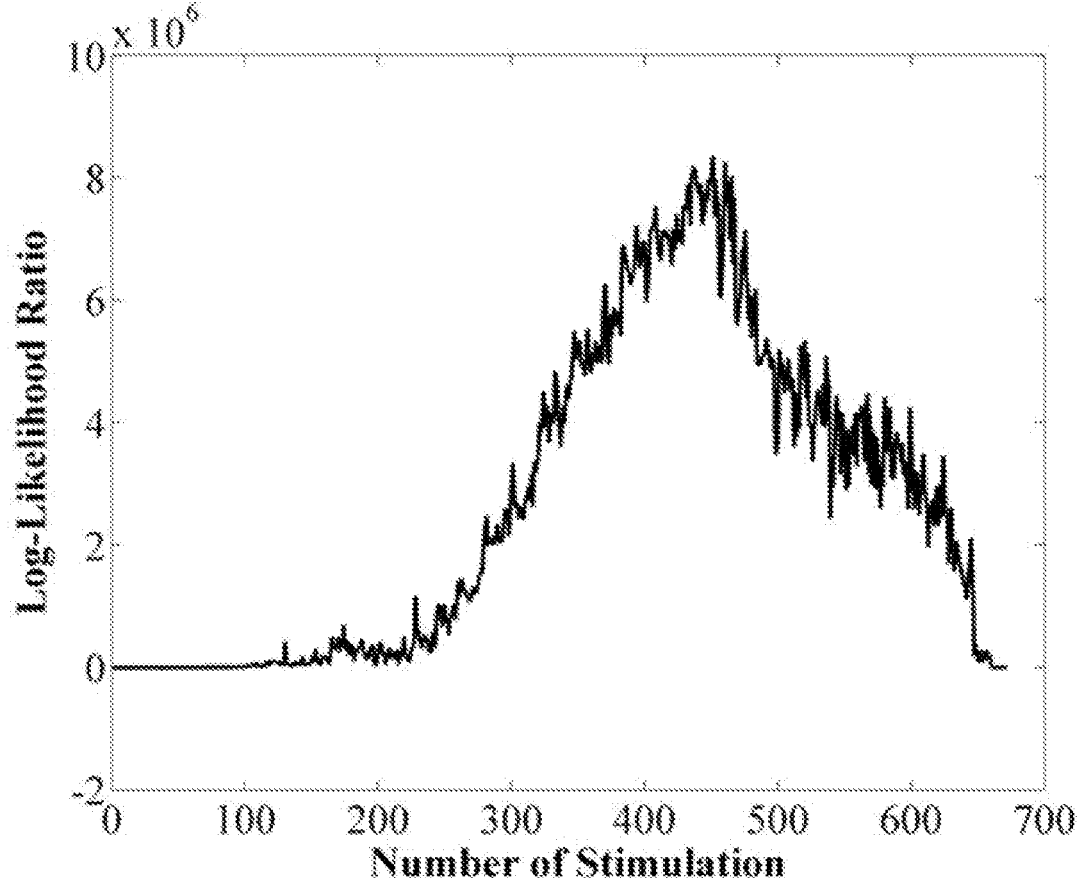

Eq. 2.4 is used to calculate one value for each segment of the signal that represents the highest statistical difference between that segment and the background noise (FIG. 4D).

In the third phase of the algorithm, a dynamic threshold h is calculated for each EMG signal in order to find the first segment of the signal that includes evoked potential and its corresponding stimulation intensity $V_{s0}$. In comparison, traditional AGLR uses a constant threshold. Based on the experimental observations, the first event corresponding to the lowest stimulation voltage does not usually trigger any muscle activation and can be considered as baseline. Consequently, the threshold value h can be computed as the summation of maximum and standard deviation of the set of $S_i$ that belongs to the baseline (Eq. 2.5).

$$h = S_{max} + \sigma_{S_i} \qquad \text{Equation 2.5}$$

All the steps of the activation detection method are demonstrated in FIG. 4 (Algorithm III, below).

---

Algorithm III: Activation detection using AGLR method

---

Select the background noise as the first non-zero segment of the de-noised EMG signal
Estimate the Gaussian distribution parameters $\sigma_o$ and $\mu_o$ (use MATLAB mle function or equivalent)
For each segment of the de-noised signal use mle function to estimate the Gaussian distribution parameters $\sigma_i$ and $\mu_i$
Calculate $S_i$ using Eq. 2.4 for all segments i of the de-noised signal
Select the baseline as the first event of the de-noised EMG signal
Calculate $S_{max}$ and $\sigma_{S_i}$ for the selected baseline to find the activation threshold h using Eq. 2.5
Compare each $S_i$ with h: If $S_i$ > h, detect the evoked potential in the $i^{th}$ segment and represent it with 1, else there is no evoked potential and represent it with 0
If 50% of the segments inside one event is active call the whole event active, else call it inactive
Repeat for all events
Find the corresponding stimulation intensity to the first active event and assign it as the voltage threshold
Repeat for all muscles

---

2.2.4 Feature Extraction

Figure 5A:
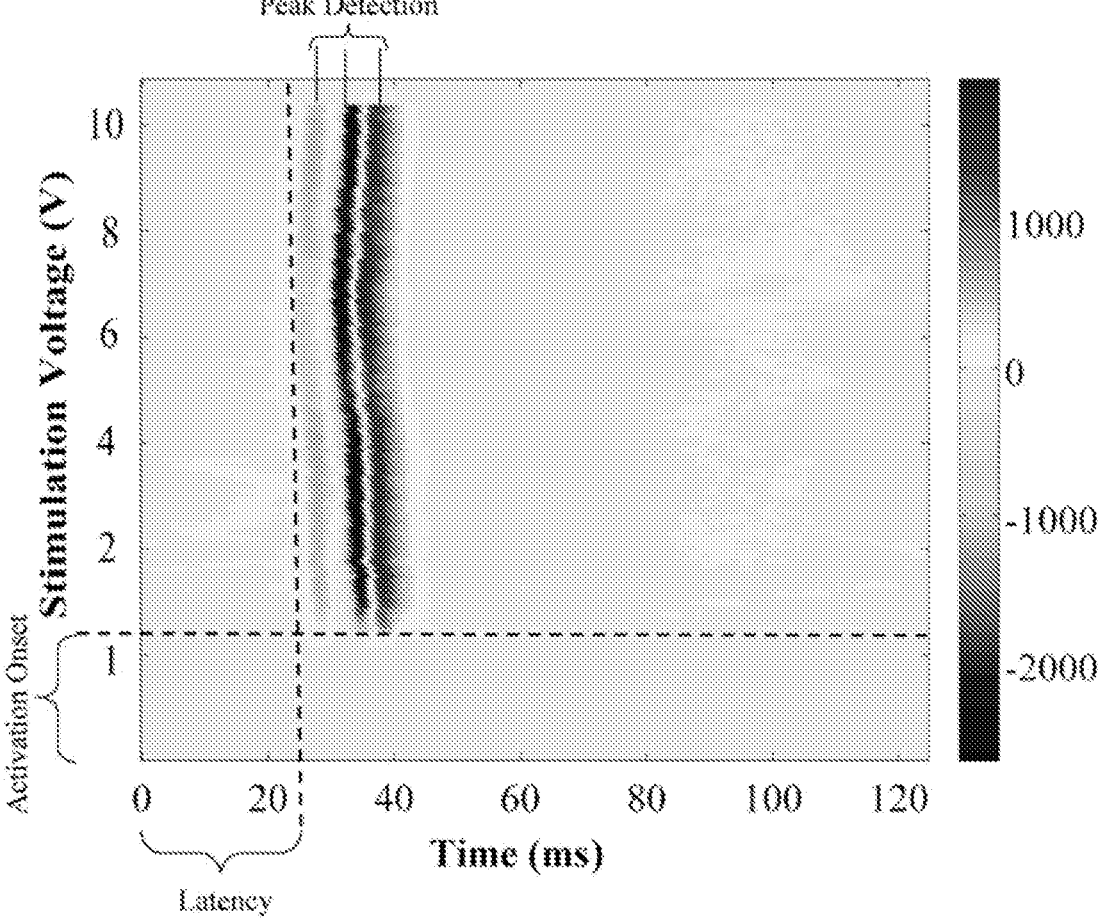
FIGS. 5A-B depict selected feature parameters of the EMG activation signal.
Figure 5B:
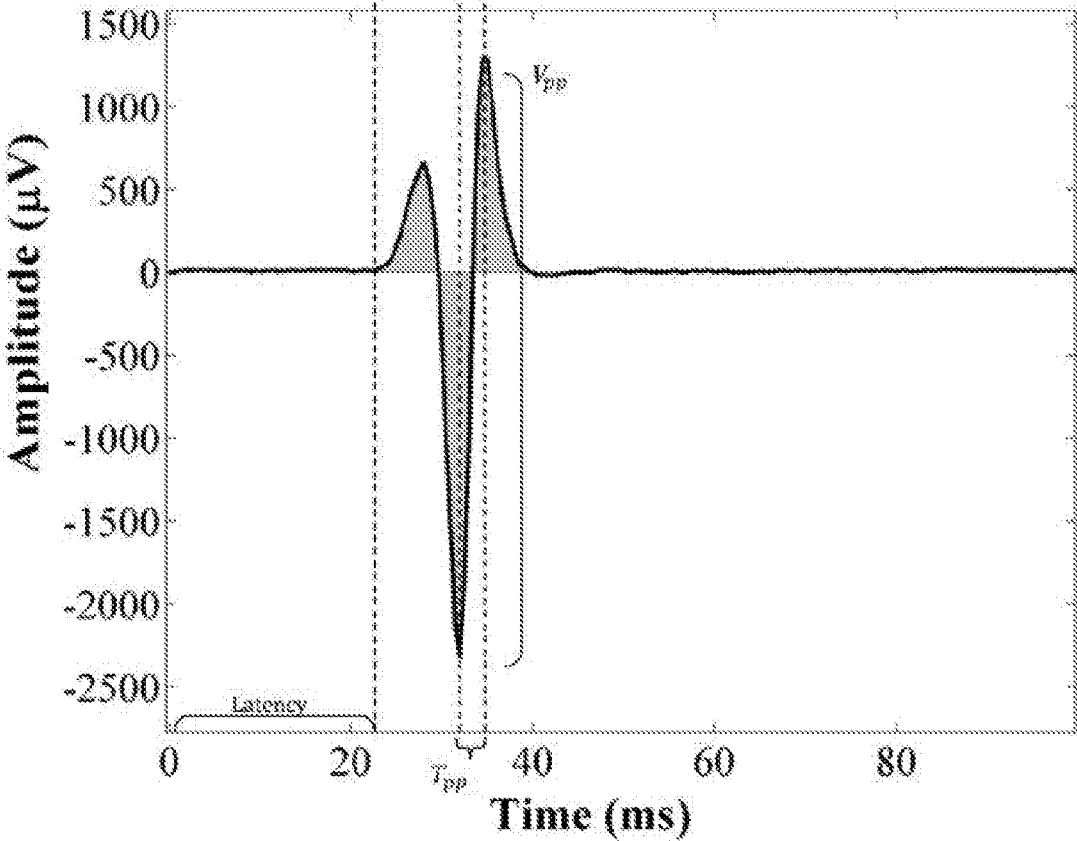

The objective of this step is to represent each potential evoked by scES with a set of features that offers the essential characteristics of that evoked potential. As a result, several parameters are selected for the EMG fragments that were segmented in the previous step. These parameters can be calculated automatically or observed visually using the 2-D representation of the EMG signal. Parameters such as activation latency, overall onset of muscle activations and number of peaks of the evoked potentials are observable parameters from 2-D image demonstration of the EMG signal (FIG. 5A). The calculated parameters in this framework are: Peak-to-peak value, which is the absolute value of the difference between the highest and the lowest peaks in the signal and its normalized value based on the highest peak between left and right muscle; Activation latency, the time interval between the stimulus timing and the onset of muscle activation; Time interval between minimum and maximum values, the time interval between the highest and lowest peak; Integrated EMG value, the area under the motor unit curvature after rectifying (taking the absolute value of) the EMG signal; and binary 0/1 values: an indication of the absence or presence of evoked potentials in each segment of the signal (Algorithm IV, below). The aforementioned features are illustrated in FIG. 5B.

---

Algorithm IV: Feature extraction

---

Peak-to-peak and min-max interval:

---

Divide each segment into 8 pieces and find the maximum $A_{max}$ and minimum $A_{min}$ amplitude values inside the first piece and their corresponding timings $T_{max}$ and $T_{min}$.
Calculate the peak-to-peak value ($A_{pp} = A_{max} - A_{min}$) and min-max interval ($T_{mm} = |T_{max} - T_{min}|$) for each segment i
Repeat for all segments
Take the average over all $A_{pp}$ and $T_{mm}$ values inside one event
Repeat for all events
Repeat for all muscles
Activation latency:

---

Divide each segment, which are detected as active by Algorithm III, into 20 pieces and take the first five pieces as baseline
Apply the same method in Algorithm III to detect the onset timing of the evoked potential in each segment $L_i$
Repeat for all segments
Take the average over all $L_i$ inside one event L
Repeat for all events
Repeat for all muscles
Integrated EMG:

---

Rectify each segment of the EMG signal
Take the integral of the rectified signal $I_{EMG}$
Repeat for all segments
Take the average over all $I_{EMG}$ values inside one event
Repeat for all events
Repeat for all muscles

---

2.2.5 Visualization

Figure 6A:
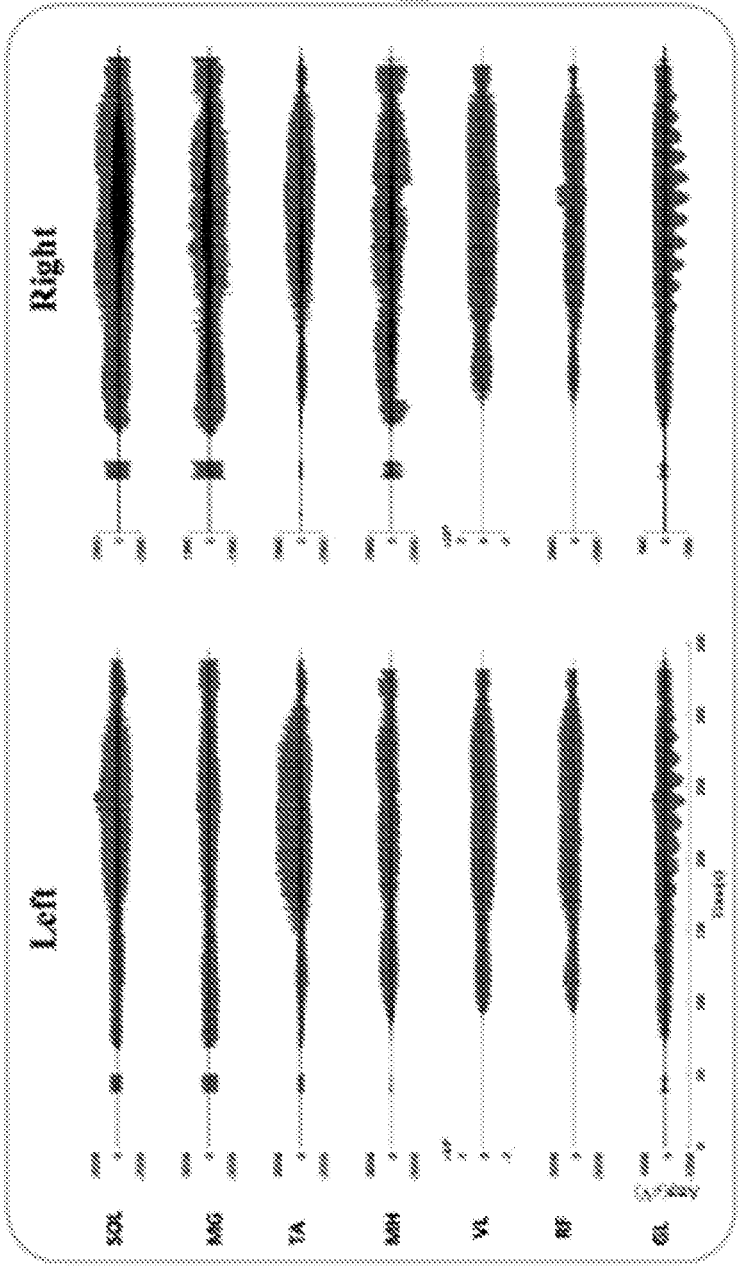
FIG. 6 depicts the conversion of 14 muscle EMG signals into Colormap images. Section A of FIG. 6 depicts raw EMG signals of 14 proximal and distal leg muscles. Section B of FIG. 6 is a Colormap image depicting the corresponding peak-to-peak values ($\mu$v) of the signals in each stimulation voltage after stimulation threshold detection. The white area in the images indicate the stimulation voltage at which the experiment began and the gray area indicates the stimulation voltages below the stimulation threshold.
Figure 6B:
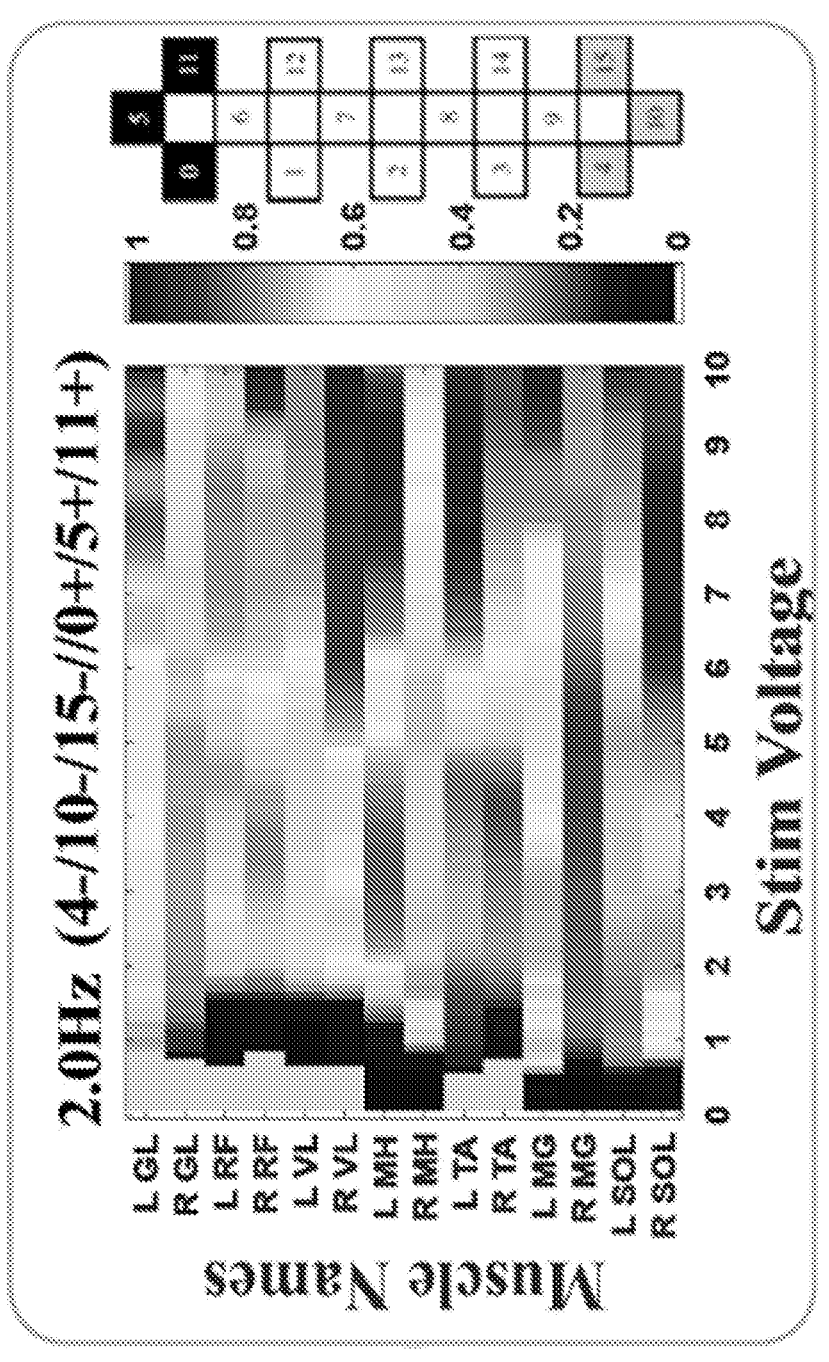
Figure 7A:
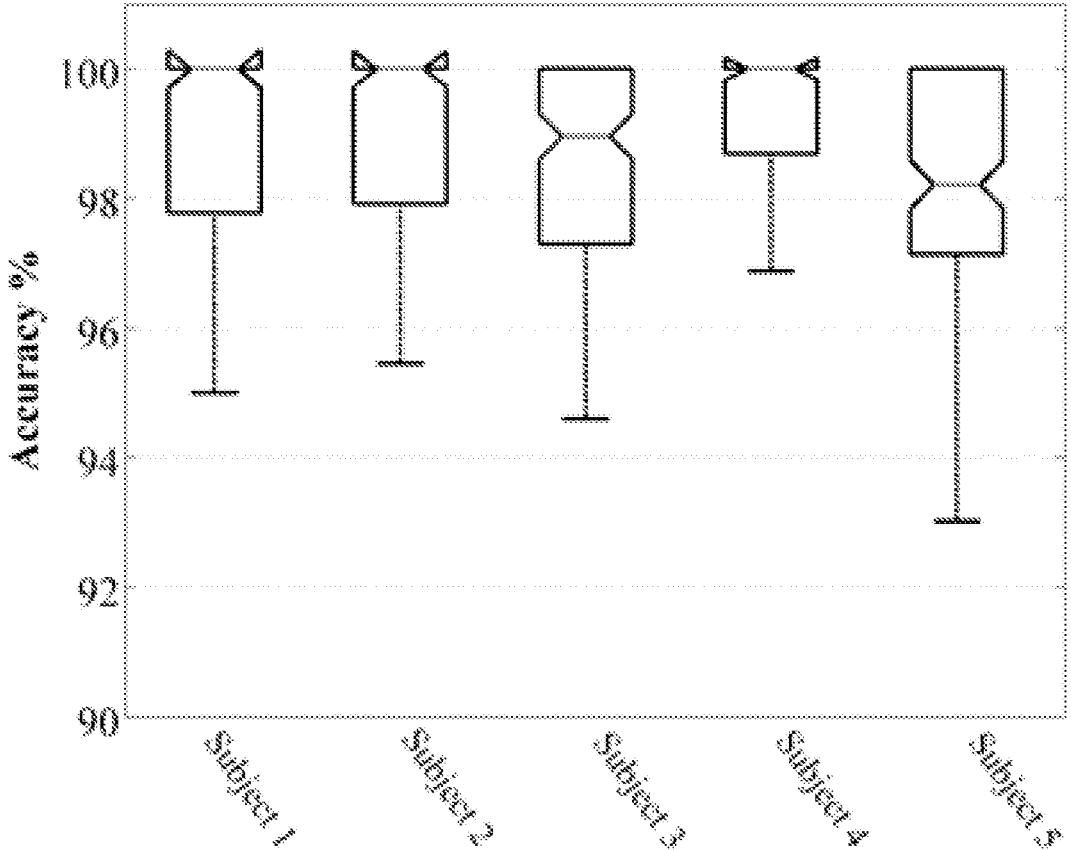
FIGS. 7A-D depict box-plot representations of performance measurements for comparing the disclosed automated activation detection method with manual detection by analysts.
Figure 7B:
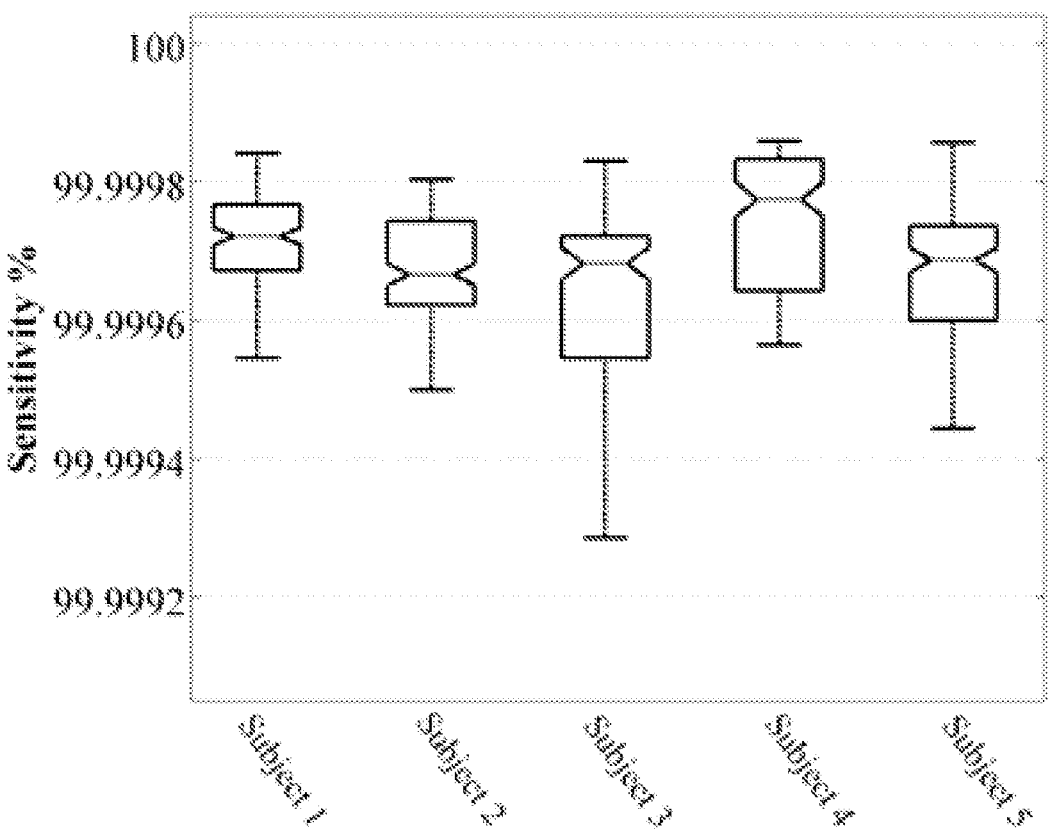
Figure 7C:
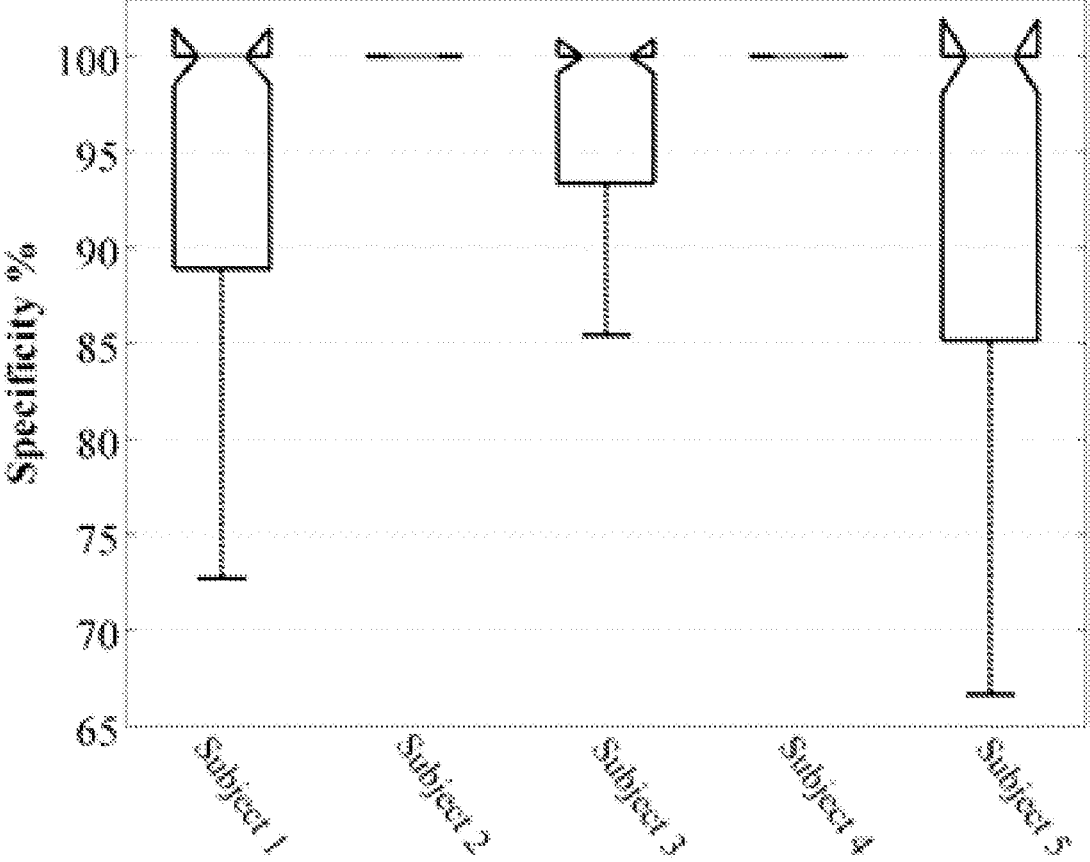
Figure 7D:
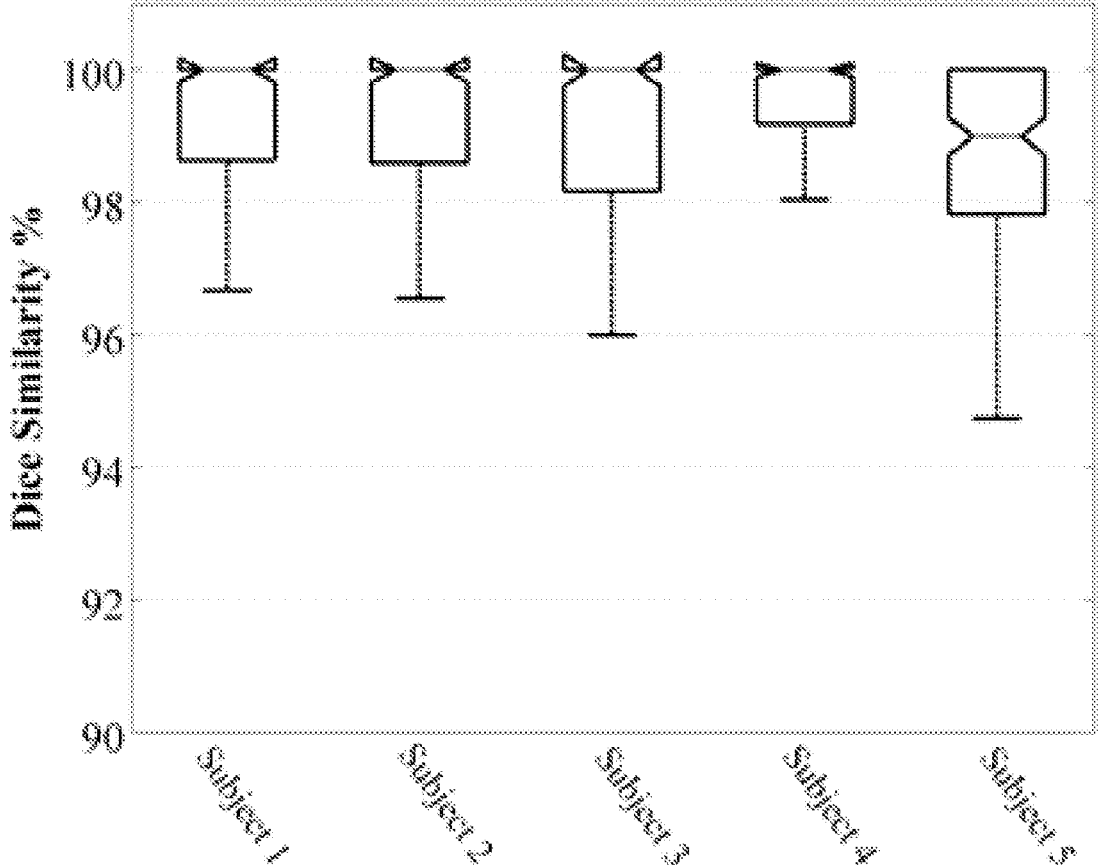

The last step of the proposed framework is to represent the data processing results in informative ways to show the connection between stimulation parameters and generated results from the computer-based method for each muscle in order to make a convenient representation for the examiner to interpret the data and modify the experiments accordingly. FIG. 6 shows the transformation of 14 EMG signals (FIG. 6A) into a single Colormap image that is showing the peak-to-peak values and the binary image that represents the binary values 0/1 that are the output of the onset detection algorithm (FIG. 6B).

Not every possible stimulation intensity is typically tested in most experimental trials, particularly voltages above the minimum voltage necessary to evoke an activation potential in a muscle. For example, in one set of experiments, testing begins by applying a low voltage and ramping up with 0.1-volt increments. Once all the muscles start to show activations, increments increase to 0.5-volts, and stimulation is applied up to 10-volts, or the highest intensity that the patient feels is comfortable. This increase in increments results in some gaps between data points corresponding to overlooked stimulation voltages. Therefore in order to maintain the continuity and resolution of the Colormap images in the visualization step, the missing values need to be interpolated based on the observed values. This task has been done using cubic smoothing spline method. Assume that there is a given set of coordinates $(x_0, y_0), (x_1, y_1), \ldots, (x_n, y_n)$ where the values of xi are in ascending order (stimulation voltages). The objective of the cubic smoothing spline method is to link the gap between adjacent points $(x_i, y_i)$, $(x_{i+1}, y_{i+1})$ using the cubic functions $P_i$; i=0, . . . , n–1; in order to piece together a curve with continuous first and second derivatives. In other words, this technique tends to preserve the values of observed data and interpolated the missing values using the piecewise curve function. The curve function also needs to satisfy the end points matching conditions. The smoothing spline method allows selection of the smoothing parameter. The smoothing parameter determines the relative weight that one would like to place on the contradictory demands of having $P_i$ be smooth (p=0), where $P_i$ is the least-squares straight line that is fitted on the data versus having $P_i$ be close to the data (p=1) so that it is variational cubic spline interpolant. In one embodiment, p=1 in order to preserve a smoothed yet accurately interpolated curves (Algorithm V, below).

| Algorithm V: Visualization |
| --- |
| Use csaps function (cubic smoothing spline) to interpolate the missing values for $A_{pp}$, $T_{mm}$, L and $I_{EMG}$<br>Assign each feature values to the corresponding stimulation intensity voltage $A_{pp}$<br>Repeat for all events<br>Repeat for all the muscles<br>Use imagesc function to visualize each matrix as Colormap image |

3 Results

In this section, the performance of the computer-based activation detection algorithm has been evaluated by comparing the output of the algorithm with the output of manually detected evoked potentials by trained data analysts as the ground truth. The proposed method was also compared with two other existing methods to show its advantages. Finally, the run-time of all the algorithms is presented.

3.1 Comparison with Manual Activation Detection

This comparison is based on calculating sensitivity, specificity, Dice similarity and accuracy as evaluation measures. These parameters are calculated based on true positive (TP), true negative (TN), false positive (FP), and false negative (FN) values. The mathematical equations for calculating these parameters and their values from comparing automatic vs. manual activation detection method on 700 EMG signals recorded from 14 leg muscles of five participants during supine experiments are presented in Table 1.

TABLE 1

Performance measurements for comparing the automated activation detection method with the manual ground truth. The five-number summary of all the calculated values are presented in this table.

|  | Total Accuracy %<br>(TP + TN)/<br>(TP + FP + TN + FN) | Total Sensitivity<br>%<br>TP/(TP + FN) | Total Specificity<br>%<br>TN/(TN + FP) | Total Dice<br>Similarity % 2TP/<br>(2TP + FN + FP) |
| --- | --- | --- | --- | --- |
| Maximum | 100.00 | 99.9999 | 99.9999 | 99.9999 |
| Upper quartile | 100.00 | 99.9998 | 99.9989 | 99.9999 |
| Median | 100.00 | 99.9997 | 99.9975 | 99.9998 |
| Lower quartile | 97.7273 | 99.9996 | 91.6659 | 98.4614 |
| Minimum | 94.3396 | 99.9994 | 79.5917 | 96.2961 |

This table shows the five-number summary of all the comparison measurements. These five values are maximum, median, upper and lower quartile, and minimum values of all the measurements (outliers are excluded). Moreover, the box-plots of all the performance measurement parameters for each individual are shown in FIG. 7. The mean and root mean square error (RMSE) of all the measurements (including outliers) are presented separated based on subjects in Table 2, and separated by muscles in Table 3.

TABLE 2

Mean and RMSE of the performance measurements for comparing the automated activation detection method with the manual ground truth as a function of subjects.

| Subject # | | 1 | 2 | 3 | 4 | 5 |
|---|---|---|---|---|---|---|
| Sensitivity | Mean | 99.8226 | 99.4128 | 99.3792 | 99.8518 | 98.8426 |
| % | RMSE | 1.2273 | 1.8114 | 1.9518 | 0.6056 | 8.7196 |
| Specificity | Mean | 93.4503 | 97.1311 | 94.7098 | 95.3723 | 92.0207 |
| % | RMSE | 11.8018 | 6.4772 | 9.6330 | 10.4982 | 11.1296 |
| Similarity | Mean | 99.0072 | 99.1890 | 97.2539 | 99.5583 | 97.6363 |
| % | RMSE | 2.6263 | 1.4585 | 7.5508 | 0.9379 | 8.6058 |
| Accuracy | Mean | 98.5775 | 98.8611 | 97.0499 | 99.2641 | 97.6272 |
| % | RMSE | 3.4938 | 1.9659 | 6.0939 | 1.5476 | 3.1851 |

TABLE 3

Mean and RMSE of the performance measurements for comparing the automated activation detection method with the manual ground truth as a function of muscles.

| | Accuracy % (TP + TN)/ (FP + FN + TP + TN) | | Dice Similarity % 2TP/(2TP + FP + FN) | | Specificity % TN/(TN + FP) | | Sensitivity % TP/(TP + FN) | |
|---|---|---|---|---|---|---|---|---|
| | Mean | RMSE | Mean | RMSE | Mean | RMSE | Mean | RMSE |
| LSOL | 99.19 | 1.80 | 97.61 | 13.50 | 97.91 | 6.50 | 97.56 | 13.93 |
| LMG | 97.33 | 6.97 | 98.39 | 5.53 | 95.56 | 10.02 | 99.04 | 2.93 |
| LTA | 98.03 | 3.45 | 97.80 | 6.25 | 95.08 | 10.43 | 99.43 | 1.83 |
| LMH | 99.01 | 1.46 | 99.38 | 0.90 | 94.46 | 11.40 | 99.78 | 0.74 |
| LVL | 98.78 | 1.70 | 99.17 | 1.18 | 93.06 | 10.59 | 99.91 | 0.62 |
| LRF | 98.82 | 1.60 | 99.20 | 1.14 | 94.49 | 9.79 | 99.71 | 0.86 |
| LGL | 96.63 | 5.94 | 97.75 | 4.37 | 87.63 | 16.06 | 99.75 | 1.02 |
| RSOL | 98.19 | 4.18 | 97.88 | 7.52 | 98.30 | 4.94 | 99.08 | 2.33 |
| RMG | 97.78 | 6.18 | 98.21 | 6.46 | 96.09 | 9.05 | 99.55 | 1.15 |
| RTA | 98.24 | 2.47 | 98.43 | 2.86 | 94.40 | 8.67 | 99.49 | 1.47 |
| RMH | 98.61 | 2.69 | 99.04 | 1.92 | 94.40 | 9.73 | 99.93 | 0.43 |
| RVL | 98.97 | 1.67 | 99.27 | 1.23 | 96.56 | 6.42 | 99.71 | 1.08 |
| RRF | 98.49 | 2.38 | 98.84 | 1.99 | 95.00 | 7.42 | 99.95 | 0.31 |
| RGL | 97.90 | 2.45 | 98.64 | 1.63 | 91.23 | 12.64 | 99.68 | 1.20 |

3.2 Comparison with Other Activation Detection Methods

The performance of proposed method was compared with two other methods: the Teager-Kaiser Energy Operation (TKEO) method and AGLR without GGMRF smoothing. The comparison is based on recorded EMG signals as well as simulated EMG signal. The simulated EMG signal was designed using an activation shape signal, X(k) that is convolved with a train of Dirac delta impulses $\Sigma_{n=1}^{k}0.01n$ $\delta(t-n)$, where the amplitudes are linearly increasing. The additive white Gaussian noise, n(t), will then be added to the signal based on the desired signal to noise ratio (SNR) to generate the final simulated signal. This signal has 50 segments, and the first 20 segments do not include any activation, and the first 10 segments are considered as baseline. One embodiment of the pseudocode of the TKEO method implementation is presented in Algorithm VI, below.

Algorithm VI: Activation detection using TKEO method

Segment the signal based on stimulation timings (similar to Algorithm I)
Calculate the TEKO value for each sample $x_{ijk}$ inside the segment
$(TKEO_{ijk} = x_{ijk}^2 - (x_{i-1jk} \cdot x_{i+1jk}))$
Repeat for all segments j
Repeat for all muscles k
Take the first event after TKEO operation as baseline -continued Algorithm VI: Activation detection using TKEO method Calculate the baseline maximum and standard deviation and find the activation threshold $h = TKEO_{base_{max}} + TKEO_{sd}$
Calculate the maximum value for the segment $TKEO_{max}$
If $TKEO_{max} > h$, detect the evoked potential in the current segment and represent it with 1, else there is no evoked potential and represent it with 0
Repeat for all segments
If 50% of the segments inside one event is active call the whole event active, else call it inactive
Repeat for all events
Find the corresponding stimulation intensity to the first active event and assign it to be the activation intensity threshold
Repeat for all the muscles The results of comparing the proposed method with regular AGLR and TKEO based on the total accuracy in the recorded EMG signals from five patients are presented in Table 4.

TABLE 4

| Comparison of methods based on five-number-summary of the total accuracy. | | | |
| --- | --- | --- | --- |
| | AGLR + GGMRF | AGLR | TKEO |
| Maximum | 100.00 | 100.00 | 100.00 |
| Upper quartile | 100.00 | 100.00 | 100.00 |
| Median | 100.00 | 98.9583 | 98.4251 |
| Lower quartile | 97.7273 | 97.4359 | 97.2222 |
| Minimum | 94.3396 | 93.6508 | 93.1818 |

As indicated in Table 4, AGLR and TKEO showed lower accuracy rates compared to the AGLR+GGMRF method disclosed herein. This shows that adding the GGMRF smoothing technique to the pre-processing step increases the effectiveness of the activation detection method.

Figure 8:
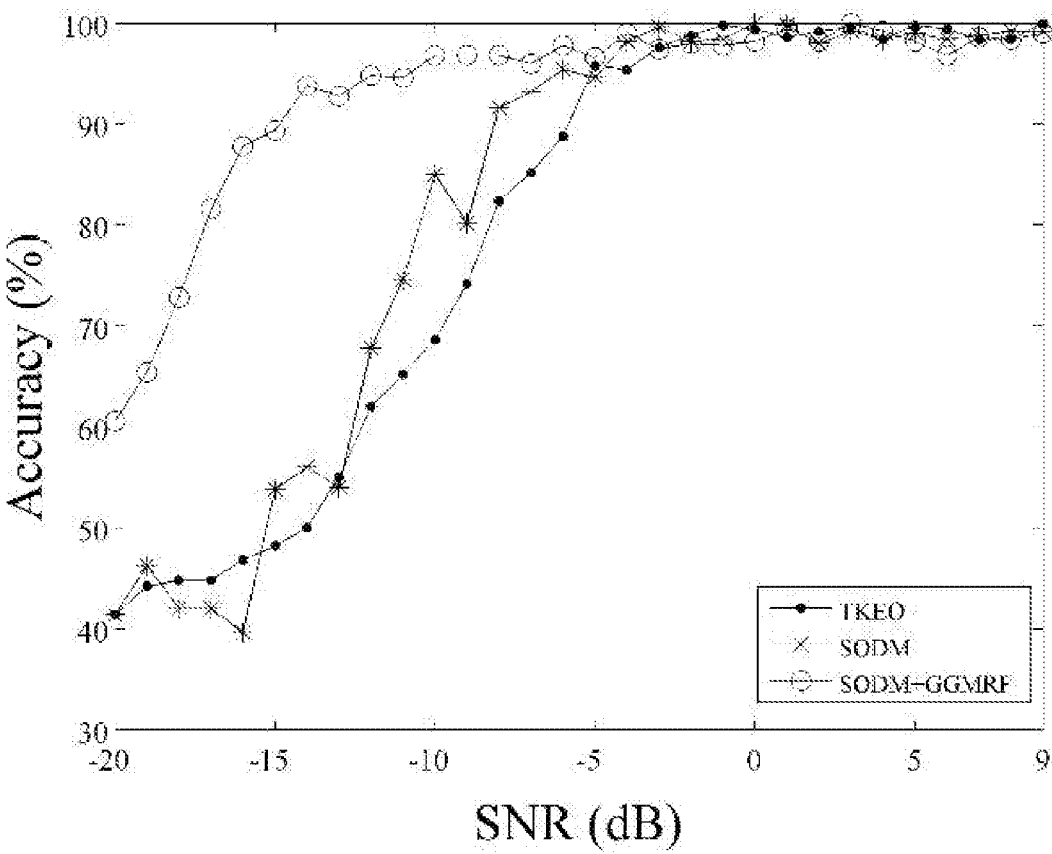
FIG. 8 is a graph depicting a comparison of three activation detection methods, TKEO, AGLR, and AGLR with GGMRF, for accuracy as an activation detection method as a function of SNR (dB).

In order to show the sensitivity of the proposed framework to SNR and to compare it with other methods, the SNR of the stimulated signal was increased from −20 to 9 dB and the accuracy measurement versus SNR plotted. The results are shown in FIG. 8. It is clear from this plot that the AGLR with GGMRF significantly outperforms other methods in signals with lower SNR values.

3.3 Calculating Total Run-Time of the Algorithms

The hardware that was used to process the EMG signals and calculate the run-time is a Dell computer, Optiplex 9020, Intel® Core™i7-4790 CPU @ 3.60 GHz, 16.0 GB RAM, 64-bit Operating System. The software is MAT-LAB™ R2011a. The run-time of the proposed framework is directly dependent on the length of the experiments. Table 5 presents the average run-time of each of five algorithms and the total time for 10 intensity ramp-up experiments with 5 to 7 minutes length.

view how different muscles respond to changes in stimulation voltage, frequency and configuration.

4 Discussion

Proposed herein is a novel framework consisting of five algorithms for activation detection and visualization of EMG signals recorded from multiple leg muscles of individuals with spinal cord injuries who have epidural stimulator implantation. Using this framework, a raw EMG signal is converted into a two/three dimensional image, the signal is de-noised using GGMRF image smoothing techniques, the occurrence of scES induced muscle activation is automatically detected, features of the muscle activation are extracted, and visual output is generated for interpretation. Each of these five novel algorithms has several advantages. For instance, the first algorithm that converts signals into images has several benefits such as clearly showing the latencies of all activations as well as the overall intensity onset of scES induced motor responses. It is also useful for the next step that is GGMRF image smoothing to get a de-noised signal without affecting the shape and latency of muscle activations. As it is shown in the results section, adding this step to the framework is also noticeably advantageous for the performance of the next step, which is the activation detection. In the activation detection algorithm, a statistically optimal decision method was developed by applying maximum likelihood estimator (MLE) together with comparing the probability density functions of the muscle activations to the background noise utilizing a log-likelihood ratio and calculating the dynamic activation threshold. In comparing the automatic method for activation threshold detection vs. manual detection (ground truth) on 700 EMG signals, the new automated approach developed here demonstrated an overall accuracy of 98.28% based on the errors of combined false positive and false negative data. It is important to note that the proposed method does not need any a priori information for the statistical model, which makes it a fully automatic method that uses only the current and previous EMG signal values to build the statistical model. Finally, the combination of modified SOD method

TABLE 5

| The run-time mean and RMSE of each steps of the proposed framework | | | | | | | |
| --- | --- | --- | --- | --- | --- | --- | --- |
| | | Converting signal to image | Noise reduction | Activation detection | Feature extraction | Visualization | Total |
| Run-time (s) | Mean | 3.9342 | 6.6107 | 1.5433 | 0.0506 | 0.4090 | 12.7167 |
| | RMSE | 1.3343 | 1.1896 | 0.2480 | 0.0069 | 0.0063 | 2.3310 |

Figure 9A:
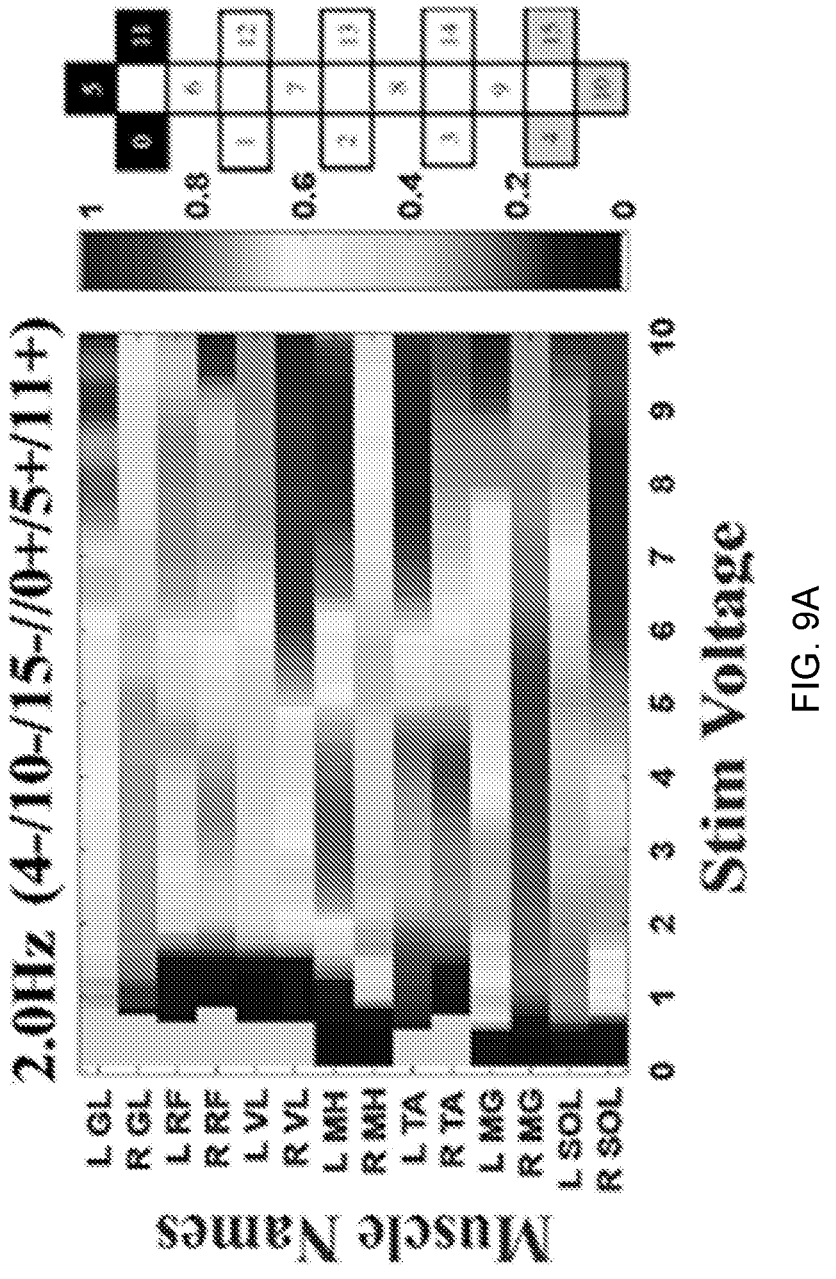
FIG. 9A-C depict Colormap images output from the disclosed method.
Figure 9B:
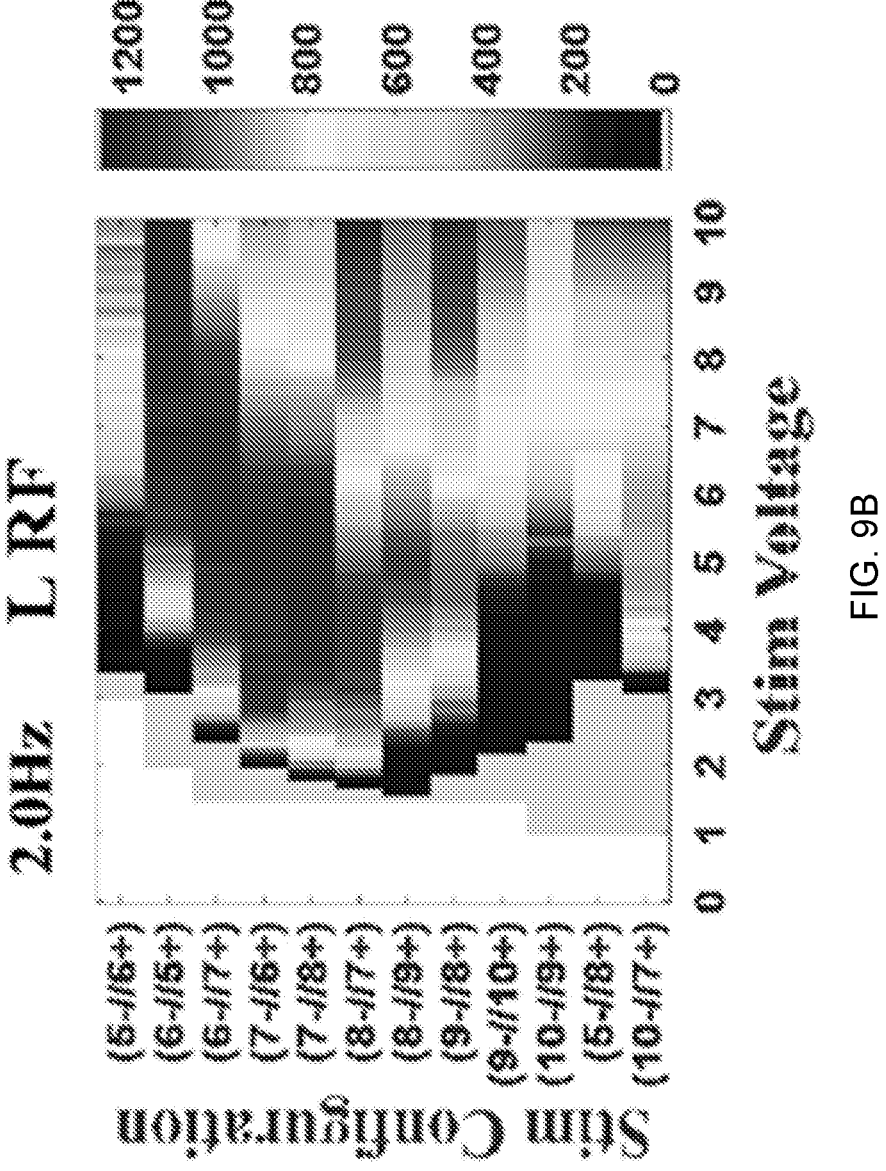
Figure 9C:
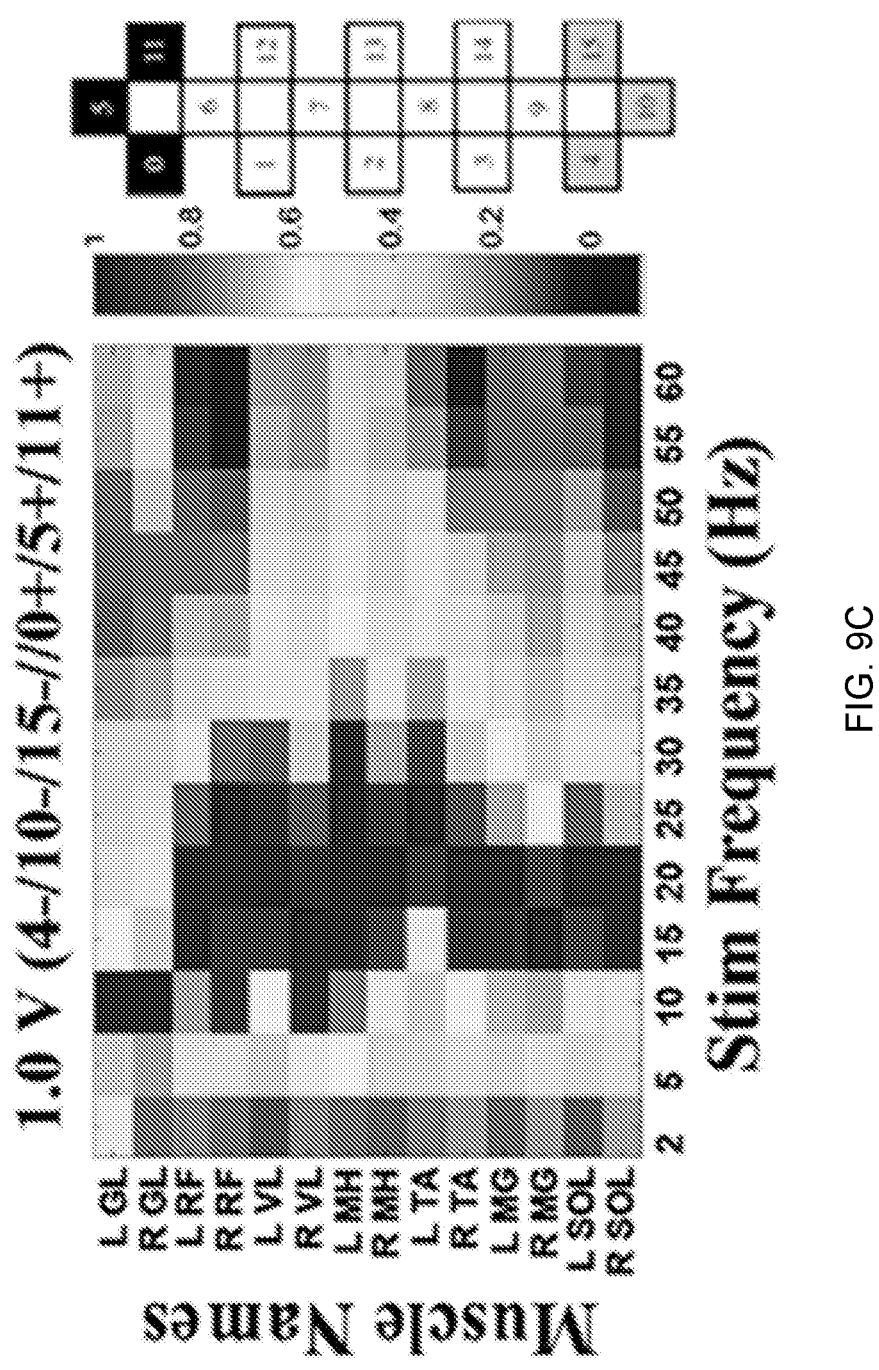

The average and standard deviation of total execution time for processing the data through all five algorithms is approximately 12.71±2.33 seconds, which compared to the previous manual methods that used to take up to several days, the disclosed automatic method is outstandingly time-efficient. Visualization of the extracted features of the evoked potentials in a visually perceptible format, specifically, colormap images, has been found to greatly aid experimentalists in their efforts to understand the effects of scES and its various parameters (voltage, frequency and electrode configuration) on the motor function of the paralyzed muscles in SCI patients. FIG. 9(A-C) displays a series of colormap images which allow an experimentalist to easily and GGMRF has proven to have minimum sensitivity to the changes in the signal to noise ratio compared to the other well-known EMG onset detection methods, i.e. SOD method without smoothing and TKEO method using both simulated EMG signal and real EMG signals. Comparing the three methods on the recorded EMG signals indicates the robustness in the accuracy of the proposed activation method in the situation where no information about the noise level in the signal is known. In addition, the feature extraction and visualization steps of the framework help analysts to make accurate and quick connections between the desired EMG features and the scES parameters like intensity voltage, configuration and frequency. In conclusion, this method clearly demonstrates the advantages of implementing a set of algorithms for improving the accuracy and speed in complex EMG data analysis.

Various aspects of different embodiments of the present invention are expressed in paragraphs X1 and X2 as follows:

X1. One aspect of the present invention pertains to a method for detection and characterization of evoked potentials in muscles, comprising recording electrical signals at least one of a patient's muscles; dividing the electrical signals into sequential segments; calculating, for each segment, a highest statistical difference Si between the electrical signal in that segment and background noise; calculating a dynamic threshold h; and detecting an evoked potential in one of the patient's muscles if Si>h in at least 50% of the segments.

X2. Another aspect of the present invention pertains to a method for detection and characterization of evoked potentials in muscles, comprising delivering a plurality of epidural stimulations to a patient at a stimulation voltage, each of the plurality of epidural stimulations separated by a time interval; recording electrical signals at least one of the patient's muscles, wherein the recording is concurrent with the delivering; dividing the electrical signals into sequential segments; calculating, for each segment, a highest statistical difference $S_i$ between the electrical signal in that segment and background noise; calculating a dynamic threshold h; determining whether $S_i$>h in at least 50% of the segments; and increasing the stimulation voltage until an evoked potential is detected; wherein the evoked potential is detected if $S_i$>h in at least 50% of the segments.

X3. A further aspect of the present invention pertains to a method for determining the location a muscle activation potential evoked from epidural stimulation and minimum voltage required to evoke activation potential, comprising delivering a plurality of epidural stimulations to a patient at a stimulation voltage; recording electrical signals at a plurality of the patient's muscles; dividing the electrical signals into sequential segments; reducing the noise of the electrical signals; calculating, for each segment, a highest statistical difference $S_i$ between the electrical signal in that segment and background noise; calculating a dynamic threshold h; determining whether $S_i$>h in at least 50% of the segments; and increasing the stimulation voltage until an activation potential is detected in one of the plurality of muscles, wherein the activation potential is detected if $S_i$>h in at least 50% of the segments.

Yet other embodiments pertain to any of the previous statements X1 or X2 which are combined with one or more of the following other aspects.

Wherein the method further comprises delivering a plurality of epidural stimulations to the patient's spinal cord at a first stimulation voltage, each of the plurality of epidural stimulations separated by a time interval.

Wherein the delivering and the recording occur concurrently.

Wherein each of the sequential segments has a duration equal to the time interval.

Wherein each segment temporally overlaps with delivery of one of the plurality of epidural stimulations.

Wherein the electrical signals are electromyography signals.

Wherein the method further comprises reducing the noise of the electrical signals.

Wherein reducing the noise comprises converting each electrical signal into a 2-D image; and applying an image smoothing method to the 2-D image to reduce signal noise.

Wherein the 2-D image comprises a plurality of pixels, each pixel having a value corresponding to an amplitude of the evoked potential, and wherein applying the image smoothing method to the 2-D image comprises recalculating the value of each pixel in the 2-D image using the following equation $$\hat{\delta}_s = \underset{\delta_s}{\text{argmin}} \left\{ |\delta_s - \tilde{\delta}_s|^q + \sigma^q \lambda^p \sum_{r \in v_s} b_{s,r} |\hat{\delta}_s - \delta_r|^p \right\}$$

Wherein the 2-D image comprises a plurality of pixels, each pixel having a value corresponding to an amplitude of the evoked potential, and wherein applying the image smoothing method to the 2-D image comprises recalculating the value of each pixel in the 2-D image using a 2-D generalized Gaussian Markov Random Field model.

Wherein an event is delivery of a plurality of epidural stimulations at a stimulation voltage.

Wherein a plurality of events are applied to a patient, each event including a different stimulation voltage.

Wherein a plurality of events are applied to a patient, each event including increasing stimulation voltages.

Wherein a baseline is a first event applied to a patient

Wherein Si is determined by $$S_i = \sum_{k=j}^{N_i} s_k = (N_i - j + 1) \ln\left(\frac{\sigma_0}{\sigma_i}\right) + \frac{(N_i - j)}{2}\left(\frac{\sigma_i^2}{\sigma_0^2} - 1\right).$$

Wherein $\sigma_i$ is an estimated standard deviation.

Wherein $N_i$ is at least 5.

Wherein h is determined by $$h = S_{max} + \sigma_{S_i}$$

Wherein $S_{max}$ is a maximum deviation of the set $S_i$ of the baseline.

Wherein $\sigma_{Si}$ is a standard deviation of the set $S_i$ of the baseline.

Wherein the baseline is the lowest stimulation voltage event.

Wherein the method further comprises delivering a plurality of epidural stimulations to the patient's spinal cord at a first stimulation voltage, followed by delivering a plurality of epidural stimulations to the patient's spinal cord at a second stimulation voltage, wherein the second stimulation voltage is unequal to the first stimulation voltage.

Wherein the second stimulation voltage is higher than the first stimulation voltage.

Wherein the method further comprises extracting at least one feature of the evoked potential.

Wherein the method further comprises extracting at least one feature of the activation potential.

Wherein the feature is one of a peak-to-peak interval, a min-max interval, an activation latency, and an integrated EMG.

Wherein the method further comprises displaying the at least one feature in a visually perceptible format.

Wherein the visually perceptible format is a colormap image.

Wherein recording electrical signals at least one of the patient's muscles includes recording electrical signals at a plurality of the patient's muscles, and wherein detecting an evoked potential in one of the patient's muscles includes associating the evoked potential with one of the patient's muscles in the plurality of the patient's muscles.

The foregoing detailed description is given primarily for clearness of understanding and no unnecessary limitations are to be understood therefrom for modifications can be made by those skilled in the art upon reading this disclosure and may be made without departing from the spirit of the invention.

What is claimed is:

1. A method for detection and characterization of evoked potentials in muscles, comprising:

recording electrical signals from a plurality of a patient's muscles;

dividing the electrical signals into sequential segments;

reducing the noise of the electrical signals, wherein reducing the noise comprises converting each electrical signal into a 2-D image and applying an image smoothing method to the 2-D image to reduce signal noise;

calculating, for each segment, a highest statistical difference $S_i$ between the electrical signal in that segment and background noise;

calculating a dynamic threshold h; and detecting an evoked potential in the plurality of the patient's muscles if $S_i > h$ in at least 50% of the segments; and wherein detecting the evoked potential in the plurality of the patient's muscles includes localizing the evoked potential in one muscle in the plurality of the patient's muscles.

2. The method of claim 1, further comprising delivering a plurality of epidural stimulations to the patient's spinal cord at a first stimulation voltage, each of the plurality of epidural stimulations separated by a time interval.

3. The method of claim 2, wherein the delivering and the recording occur concurrently.

4. The method of claim 2, wherein each of the sequential segments has a duration equal to the time interval.

5. The method of claim 2, wherein each segment temporally overlaps with delivery of one of the plurality of epidural stimulations.

6. The method of claim 1, wherein the electrical signals are electromyography signals.

7. The method of claim 1, wherein $S_i$ is determined by $$S_i = \sum_{k=j}^{N_i} s_k = (N_i - j + 1)\ln\left(\frac{\sigma_0}{\sigma_i}\right) + \frac{(N_i - j)}{2}\left(\frac{\sigma_i^2}{\sigma_0^2} - 1\right).$$

8. The method of claim 1, wherein h is determined by $$h = S_{max} + \sigma_{S_i}.$$

9. The method of claim 1, further comprising delivering a plurality of epidural stimulations to the patient's spinal cord at a first stimulation voltage, followed by delivering a plurality of epidural stimulations to the patient's spinal cord at a second stimulation voltage, wherein the second stimulation voltage is unequal to the first stimulation voltage.

10. The method of claim 9, wherein the second stimulation voltage is higher than the first stimulation voltage.

11. The method of claim 1, further comprising extracting at least one feature of the evoked potential.

12. The method of claim 11, wherein the feature is one of a peak-to-peak interval, a min-max interval, an activation latency, and an integrated EMG.

13. The method of claim 11, further comprising displaying the at least one feature in a visually perceptible format.

14. The method of claim 13, wherein the visually perceptible format is a colormap image.

15. The method of claim 1, wherein the image smoothing method is a Gaussian Markov Random Field model.

16. A method for detection and characterization of evoked potentials in muscles, comprising:

delivering a plurality of epidural stimulations to a patient at a stimulation voltage, each of the plurality of epidural stimulations separated by a time interval;

recording electrical signals from a plurality of the patient's muscles, wherein the recording is concurrent with the delivering;

dividing the electrical signals into sequential segments;

reducing the noise of the electrical signals, wherein reducing the noise comprises converting each electrical signal into a 2-D image and applying an image smoothing method to the 2-D image to reduce signal noise;

calculating, for each segment, a highest statistical difference $S_i$ between the electrical signal in that segment and background noise;

calculating a dynamic threshold h;

determining whether $S_i > h$ in at least 50% of the segments; and increasing the stimulation voltage until an evoked potential is detected; and localizing the evoked potential in one of the patient's muscles in the plurality of the patient's muscles;

wherein the evoked potential is detected if $S_i > h$ in at least 50% of the segments.

17. The method of claim 16, further comprising extracting at least one feature of the evoked potential.

18. The method of claim 17, wherein the feature is one of a peak-to-peak interval, a min-max interval, an activation latency, and an integrated EMG.

19. The method of claim 16, wherein the image smoothing method is a Gaussian Markov Random Field model.

20. A method for determining the location of a muscle activation potential evoked from epidural stimulation and minimum voltage required to evoke activation potential, comprising:

delivering a plurality of epidural stimulations to a patient at a stimulation voltage;

recording electrical signals from a plurality of the patient's muscles;

dividing the electrical signals into sequential segments;

reducing the noise of the electrical signals, wherein reducing the noise comprises converting each electrical signal into a 2-D image and applying an image smoothing method to the 2-D image to reduce signal noise;

calculating, for each segment, a highest statistical difference $S_i$ between the electrical signal in that segment and background noise;

calculating a dynamic threshold h;

determining whether $S_i > h$ in at least 50% of the segments;

increasing the stimulation voltage until an activation potential is detected in one of the plurality of muscles, wherein the activation potential is detected if $S_i > h$ in at least 50% of the segments; and localizing the evoked potential in one of the patient's muscles in the plurality of the patient's muscles.

* * * * *